(12) United States Patent
Tweedie et al.

(10) Patent No.: US 11,961,606 B2
(45) Date of Patent: Apr. 16, 2024

(54) SYSTEMS AND METHODS FOR PROCESSING MEDICAL IMAGES FOR IN-PROGRESS STUDIES

(71) Applicant: Blackford Analysis Ltd., Edinburgh (GB)

(72) Inventors: Robert John Tweedie, Edinburgh (GB); Paul Henderson, Klosterneuburg (AT); Keith Houston, Birmingham (GB)

(73) Assignee: BLACKFORD ANALYSIS LTD., Edinburgh (GB)

( * ) Notice: Subject to any disclaimer, the term of this patent is extended or adjusted under 35 U.S.C. 154(b) by 133 days.

(21) Appl. No.: 16/695,642

(22) Filed: Nov. 26, 2019

(65) Prior Publication Data

US 2021/0158931 A1    May 27, 2021

(51) Int. Cl.
*G16H 30/20* (2018.01)
*G06F 16/14* (2019.01)
(Continued)

(52) U.S. Cl.
CPC ............ *G16H 30/20* (2018.01); *G06F 16/14* (2019.01); *G06F 40/40* (2020.01); *G16H 10/20* (2018.01); *G16H 30/00* (2018.01); *G16H 30/40* (2018.01); *G16H 40/00* (2018.01); *H04L 67/12* (2013.01); *G06T 2210/41* (2013.01); *G06V 2201/03* (2022.01); *G16H 10/60* (2018.01); *G16H 80/00* (2018.01)

(58) Field of Classification Search
CPC ........... G06F 16/50; G06F 16/51; G06K 9/00; G06K 2209/05; G16H 10/20; G16H 30/20; G16H 40/00; G16H 40/67; G16H 50/70; H04L 67/12; H04N 1/2179; H04N 1/00209; H04N 1/32128; H04N 2201/0087; H04N 2201/0089
See application file for complete search history.

(56) References Cited

U.S. PATENT DOCUMENTS 9,390,153 B1    7/2016    Tochilnik
10,296,712 B2 *  5/2019   Revell ................... G16H 50/70
(Continued)

FOREIGN PATENT DOCUMENTS

WO    2014/085918 A4    6/2014
WO    2018/204698 A1    11/2018

OTHER PUBLICATIONS

Wayback Machine, Wikipedia, "Metadata", Nov. 25, 2019, Wikipedia, pp. 1-14 (Year: 2019).*

(Continued)

*Primary Examiner* — Jonathan Ng
*Assistant Examiner* — Hunter J Rasnic
(74) *Attorney, Agent, or Firm* — THE MARBURY LAW GROUP, PLLC

(57) ABSTRACT

A system and method for processing a plurality of medical images using a plurality of clinical applications. A current study is received by a first server, the current study having first image series metadata. The first server can determine, based on several different techniques, that the current study is in progress. The system and method generates an assembled study set comprising the current study that is processed using a clinical application, the current study having a first series and a second series.

30 Claims, 26 Drawing Sheets

(51) Int. Cl.
*G06F 40/40* (2020.01)
*G16H 10/20* (2018.01)
*G16H 30/00* (2018.01)
*G16H 30/40* (2018.01)
*G16H 40/00* (2018.01)
*G16H 80/00* (2018.01)
*H04L 67/12* (2022.01)
*G16H 10/60* (2018.01)

(56) References Cited

U.S. PATENT DOCUMENTS

| | | | | |
|---|---|---|---|---|
| 10,698,981 | B2* | 6/2020 | Bhatia | G06K 9/00 |
| 10,795,927 | B2 | 10/2020 | Kobozev et al. | |
| 2002/0019751 | A1* | 2/2002 | Rothschild | H04N 1/00212 |
| | | | | 705/3 |
| 2002/0091659 | A1 | 7/2002 | Beaulieu et al. | |
| 2004/0141661 | A1* | 7/2004 | Hanna | G16H 80/00 |
| | | | | 707/999.107 |
| 2005/0027995 | A1* | 2/2005 | Menschik | G16H 40/67 |
| | | | | 713/193 |
| 2005/0206967 | A1 | 9/2005 | Viswanth et al. | |
| 2006/0139318 | A1 | 6/2006 | Kariathungal et al. | |
| 2006/0242144 | A1 | 10/2006 | Esham et al. | |
| 2006/0242159 | A1* | 10/2006 | Bishop | G16H 40/67 |
| 2008/0119717 | A1 | 5/2008 | Profio et al. | |
| 2008/0140454 | A1* | 6/2008 | Hernandez | G16H 30/20 |
| | | | | 705/3 |
| 2008/0140723 | A1 | 6/2008 | Hernandez et al. | |
| 2009/0103789 | A1* | 4/2009 | Danner | G16H 30/20 |
| | | | | 382/128 |
| 2009/0287505 | A1* | 11/2009 | Wood | G16H 10/60 |
| | | | | 705/3 |
| 2011/0010192 | A1* | 1/2011 | Backhaus | G16H 40/67 |
| | | | | 705/2 |
| 2011/0110568 | A1* | 5/2011 | Vesper | G06Q 10/10 |
| | | | | 382/128 |
| 2012/0041786 | A1* | 2/2012 | Yu | G16H 40/67 |
| | | | | 705/3 |
| 2012/0197619 | A1* | 8/2012 | Namer Yelin | G16H 50/50 |
| | | | | 382/128 |
| 2012/0323593 | A1* | 12/2012 | Backhaus | G16H 80/00 |
| | | | | 705/2 |
| 2014/0114672 | A1 | 4/2014 | Wright et al. | |
| 2014/0115020 | A1* | 4/2014 | Colaco | G06F 16/182 |
| | | | | 707/827 |
| 2014/0142980 | A1* | 5/2014 | Revell | G06F 16/50 |
| | | | | 705/3 |
| 2014/0278530 | A1* | 9/2014 | Bruce | G16H 30/20 |
| | | | | 705/3 |
| 2014/0324469 | A1* | 10/2014 | Reiner | G16H 50/70 |
| | | | | 705/3 |
| 2014/0330855 | A1 | 11/2014 | Atanasiu et al. | |
| 2015/0161329 | A1 | 6/2015 | Mabotuwana et al. | |
| 2016/0378917 | A1* | 12/2016 | Sharafshahi | G16H 30/20 |
| | | | | 705/2 |
| 2017/0185713 | A1* | 6/2017 | Bhatia | G16H 30/20 |
| 2017/0186161 | A1* | 6/2017 | Taylor | G16H 30/20 |
| 2018/0330828 | A1* | 11/2018 | Hayter, II | G16H 30/20 |
| 2018/0342314 | A1 | 11/2018 | Tichy et al. | |
| 2019/0057767 | A1* | 2/2019 | Wilson | G16H 40/40 |
| 2019/0065763 | A1 | 2/2019 | Berg | |
| 2019/0180862 | A1 | 6/2019 | Wisser et al. | |
| 2020/0051676 | A1 | 2/2020 | Hombal et al. | |
| 2020/0251218 | A1 | 8/2020 | Stoval, III et al. | |
| 2021/0313077 | A1* | 10/2021 | Smurro | G16H 50/20 |
| 2022/0140840 | A1* | 5/2022 | Wang | H03M 7/3064 |
| | | | | 707/693 |

OTHER PUBLICATIONS

"DICOM", Nov. 20, 2019, Wikipedia, Wikipedia (Year: 2019).*
International Search Report and Written Opinion dated Feb. 23, 2021 in International Patent Application No. PCT/EP2020/083558 (12 pages).
International Search Report and Written Opinion dated Feb. 25, 2021 in International Patent Application No. PCT/EP2020/083557 (11 pages).
Harris et al., "Signify Research Show Report from RSNA 2018", Signify Research Knowledge Centre, Dec. 2018 (12 pages).
Written Opinion dated Nov. 2, 2021 in International Patent Application No. PCT/EP2020/083557 (11 pages).
Non-final Office Action and Notice of References Cited dated Jul. 27, 2022 in U.S. Appl. No. 16/695,612 (17 pages).
Final Office Action and Notice of References Cited dated Feb. 2, 2023 in corresponding U.S. Appl. No. 16/695,612 (26 pages).
European Extended Search Report dated Dec. 21, 2022 in corresponding European Patent Application No. 22176868.2 (88 pages).
Gale, et al. "DICOM Modality Worklist: an essential component in a PACS environment", Journal of Digital Imaging, the Journal of the Society for Computer Applications in Radiology, vol. 13, No. 3, pp. 101-108, (Aug. 1, 2000).
"Spoke-hub distribution paradigm", Wikipedia, https://en.wikipedia.org/w/index.php?title=Spoke-hub_distribution_paradigm&oldid=909118070, 5 pages, (Aug. 3, 2019).
National Electrical Manufacturers Association, "Official Standard—Digital Imaging and Communications in Medicine (DICOM)—Part 6: Data Dictionary", URL:https://dicom.nema.org/medical/dicom/1998/publish/98_06pu.pdf, 62 pages, (Dec. 12, 2022).
Advisory Action dated Apr. 6, 2023 in corresponding U.S. Appl. No. 16/695,612 (10 pages).

* cited by examiner

```
<relevanceMap>
        <study
                name='{string}'
                description='{regularExpression}'
                containedModalities='{commaSeparatedStringList}'
                minimumInstanceCount='{integer}'
                priors='{commaSeparatedStringList}'
                priority='{integer}'>
                <series
                        name='{string}'
                        bodyPartExamined='{regularExpression}'
                        description='{regularExpression}'
                        minimumInstanceCount='{integer}'
                        modality='{string}'
                        seriesNumber='{string}'
                        action='{string}'/>
        </study>
        <!-- More study rules here as required -->
</relevanceMap>
```

```
<study name="LEXT-CT" containedModalities="CT"
 description="(LO|LWR|LOWER).*(EX|EXT|EXTREM)|(EX|EXT|EXTREM).*(LO|LWR|LOWER)"
 priors="LEXT-CT,AOFF-CT">
      <series name="CT series" modality="CT" minimumInstanceCount="0" action="register"/>
      <series name="PT series" modality="PT" minimumInstanceCount="0" action="volumise"/>
      <series name="REG series" modality="REG" minimumInstanceCount="1" action="register"/>
</study>
```

```xml
<relevanceMap>

<study name="HDNK-CT" containedModalities="CT"
          description="CT TRAUMA 3D MULTIPLANAR"
          priors="HDNK-CT,HDNK-MR,CSPN-CT,NECK-CT-MR,SINU-CT-MR">
          <series name="CT series" modality="CT" minimumInstanceCount="0" action="register"/>
          <series name="PT series" modality="PT" minimumInstanceCount="0" action="volumise"/>
          <series name="REG series" modality="REG" minimumInstanceCount="1" action="register"/>
        </study>

<study name="LIVER-CT" containedModalities="CT"
          description="ABLATION|LIVER|HEPATIC"
          priors="LIVER-CT,CABP-CT,CABD-CT,ABPL-CT,PELV-CT,PANC-CT,GU-CT">
          <series name="CT series" modality="CT" minimumInstanceCount="0" action="register"/>
          <series name="PT series" modality="PT" minimumInstanceCount="0" action="volumise"/>
          <series name="REG series" modality="REG" minimumInstanceCount="1" action="register"/>
        </study>

<study name="ABPL-CT" containedModalities="CT"
          description="ABSCESS DRAIN|ENTER|CYSTOGRAM|PERITONEAL"
          priors="ABPL-CT,PELV-CT,ABD-CT, ">
          <series name="CT series" modality="CT" minimumInstanceCount="0" action="register"/>
          <series name="PT series" modality="PT" minimumInstanceCount="0" action="volumise"/>
          <series name="REG series" modality="REG" minimumInstanceCount="1" action="register"/>
        </study>

</relevanceMap>
```

Study Matching Rule

Clinical Application: Registration

Rule name: LIVER-CT    Rule Priority: 0

Modalities: ○ any
⦿ restricted  CT  none  none  none

Study Description: ABLATION | LIVER | HEPATIC
(exact, or regular expression)

Other DICOM fields: Referring Physician's Name | JONES    delete
                                                          Create New Priors Rules: ○ all study rules for this clinical application
⦿ named rules: LIVER-CT, CABP-CT, CABD-CT, ABPL-CT Series Rules:
| Rule Name | Action | |
|---|---|---|
| CT series | 0 | edit |
| PT series | 0 | edit |
| REG series | 0 | edit |

Create New

Cancel   Save

SYSTEMS AND METHODS FOR PROCESSING MEDICAL IMAGES FOR IN-PROGRESS STUDIES

FIELD

The described embodiments relate to the processing of medical images using a plurality of clinical software applications.

BACKGROUND

Large medical organizations have challenges in the routing of medical data between different systems involved in collecting the medical data, and clinical software applications that process and analyze the medical data. This is particularly challenging due to the fact that medical images may be very large. Furthermore, the medical organization may have many different information systems implemented to process data.

Medical data is collected about a patient when they are imaged at an image acquisition device, and the medical data includes image data and associated image acquisition metadata. "A Modality" refers to the categorical type of image acquisition generated by different image acquisition devices (e.g. CT, MR, x-ray, ultrasound or PET; as in, "those images have modality 'CT'"). Depending on diagnostic or clinical need and modality type, a scanning episode might capture a single image, a series of images covering one area of anatomy, or multiple series of images covering the same or different areas of anatomy, the latter for example if there are multiple modes of operation for a scanner (e.g. MR) or perhaps to cover the time before and after administration of a contrast agent. Furthermore, multiple scans may be taken of the same patient and anatomy area at different times, using the same or different image acquisition device. Finally, some image acquisition devices allow for the capture of videos of moving anatomy (e.g. a beating heart)—which herein is treated as a series of images amenable to processing.

A single patient may be imaged by an image acquisition device. The patient may visit and be imaged by the image acquisition device on multiple different occasions, and these studies may be for a planned sequence of scans to monitor a disease and/or to track treatment. This may be referred to as a longitudinal sequence of studies. At the medical provider, IT systems may be provided to store the studies and associate individual studies of the same patient with one another. However, between different IT systems (or even between different studies on the same IT system) patient medical data may not be correctly associated. It is often desirable to perform additional analysis on images after acquisition at the image acquisition device, but before presentation to clinicians. Such processing analyses have the aim of supporting a clinician's review of the scan by, for example, providing quantification of certain clinically relevant features in the images, or adding new, clinically useful, images derived in some way from the originals.

The data transformations of existing medical image routing systems may be applied uniformly to incoming study data, image data, series data, or metadata associated with the study data, image data, or series data. The processing of medical image data in existing systems is therefore not contextual and not based on the relevancy of the image data, or associated meta-data across multiple studies.

A first challenge in the medical organization is how to automatically match different studies that may be related and relevant to a particular analysis or diagnostic task. During processing using a clinical software application, it is desirable to have a complete set of all matching studies and images. Existing solutions do not adequately address the challenges faced when trying to automatically match medical data for processing by clinical software applications—for example, automatically matching and routing relevant studies with minimal human intervention.

This is further compounded after processing, since it is not obvious where the processed medical data from the clinical software application should be sent. The medical organization may have many different image acquisition devices and the input data may have come from a variety of sources.

Prior solutions allowed for workflow routing, where studies including medical data are sent from inside the medical organization to an identified clinician (or group of clinicians) at the time they need it. Such a solution, however, is not concerned with the problem of getting the right medical image data to a clinical software application that analyses the images and produces a processing result that may be associated with the medical image data.

Unlike clinician users, the clinical software applications do not move around physically, nor are they able to determine relevant or related studies to be used as input for processing. Clinician users generally select relevant or related studies to receive next from a user interface available to the clinician, and make their own decisions which data to transfer for review. Existing solutions for processing a current study and associated metadata, clinical software applications also do not determine related relevant studies, series, or image data which may be desirable for analysis alongside the current study. Clinical software applications may have significant computer resource requirements, and these resource requirements may have costs associated with their use (for example, the use of a clinical software application running on a cloud provider such as Amazon Web Services). It is therefore undesirable to process a current study with a clinical application if related and relevant studies, series, or image data is absent.

Medical images may be very large in size, and the transfer of the medical images over a network very costly. It is therefore desirable to determine relevant and related studies, series, and images using metadata associated with the medical images, to avoid unnecessary resource usage.

Clinical software applications, as discussed, produce result data, i.e. new information in addition to the original image data, and this can take the form of a new images, or additional metadata in the derived from the original images. Existing medical image processing can provide data transformations including, for example image compression and data encryption.

A second challenge faced by medical organizations when collecting a set of matching studies and images is that it is not obvious when a study received is complete. An image acquisition device may send an initial portion of a study (which may include one or more initial series, each series including image data and/or associated metadata) to a medical image archive system before one or more subsequent portions of the study (the subsequent portions may include the one or more first series and/or one or more subsequent series, each series including image data and/or associated metadata) has been collected. The initial portion of the study and the subsequent portions of the study may include a common identifier. A clinical software application may require substantial processing resources to process a matching set of studies; and if processing begins before all of the medical data is available, it may result in an incomplete processing result or it may fail completely, since the processing of the medical data by the clinical software application was performed without the second complete study for the patient. This unnecessary processing is costly to the organization.

SUMMARY

In a first aspect there is provided a method for processing a plurality of medical images using a plurality of clinical applications, the method comprising: receiving, at a first server from a first image system in the plurality of medical image systems, a current study, the current study comprising first image series metadata; determining, at the first server, that the current study is in progress; receiving, at the first server from the first image system in the plurality of medical image systems, second image series metadata corresponding to the current study; applying, at the first server, one or more relevancy matching rules of the clinical application to the current study to determine if the current study is a matched current study; receiving, at the first server from at least one medical image systems of the plurality of medical image systems, one or more matched prior studies; retrieving, at the first server, image data corresponding to the matched current study and the one or more matched prior studies; generating, at the first server, an assembled study set comprising the matched current study, the one or more matched prior studies, the image data corresponding to the matched current study, and the image data corresponding to the one or more matched prior studies; processing the assembled study set using the clinical application; and sending, from the first server to the first image system, a processed study based on the assembled study set.

In at least one embodiment, the determining, at the first server, that the current study is in progress may further comprise: receiving, one or more additional series metadata corresponding to the current study; determining, based on a count of the one or more additional series metadata corresponding to the current study, that the current study is in progress.

In at least one embodiment, the first image series metadata may be pushed to the first server from at least one of the group of a PACS server, a Modality Worklist, and a medical image device; and wherein the at least one of the group of the PACS server, the Modality Worklist, and the medical image device may push the second image series metadata.

In at least one embodiment, the determining, at the first server, that the current study is in progress may further comprise: sending, from the first server to the first image system, one or more status queries corresponding to the current study; receiving, from the first image system at the first server, one or more status responses corresponding to the one or more status queries; and determining, based on the one or more status responses, that the current study is in progress.

In at least one embodiment, the one or more status queries may comprise one or more polling requests; and the one or more polling requests may be sent from the first server to at least one of the group of a PACS server and a Modality Worklist; and the determining, based on one or more polling responses corresponding to the one or more polling requests, that the current study is in progress may be based on a change to the current study during a change threshold period of time.

In at least one embodiment, the one or more polling requests may be recurrently sent at a polling interval.

In at least one embodiment, the method may further comprise: determining, based on the polling response, that the current study has not changed at an expiry of the change threshold and that the current study is complete.

In at least one embodiment, the polling interval and the change threshold may be configurable.

In at least one embodiment, the polling interval and the change threshold may be selected based on a performance metric of the first server.

In at least one embodiment, the determining, at the first server, that the current study is in progress may further comprise: receiving, at the first server, the second image series metadata; and applying, at the first server, one or more relevancy matching rules to the second image series metadata.

In at least one embodiment, the first image series metadata may correspond to a first series of medical images collected by the first image system; the second image series metadata may corresponds to a second series of medical images collected by first image system; and the second image series metadata may be collected by the first image system after the first image series metadata is received at the first server.

In at least one embodiment, the method may further comprise: receiving, at the first server from the first image system in the plurality of medical image systems, third image series metadata corresponding to the matched current study.

In a second aspect, there is provided a system for processing a plurality of medical images using a plurality of clinical applications, the system comprising: a server, the server comprising: a memory; a network device; a processor in communication with the memory and the network device, the processor configured to: receive, at the network device from a first image system in the plurality of medical image systems, a matched current study, the matched current study comprising first image series metadata; determine that the current study is in progress; receive, at the network device from the first image system in the plurality of medical image systems, second image series metadata corresponding to the matched current study; apply one or more relevancy matching rules of the clinical application to the current study to determine if the current study is a matched current study; receive, at the network device from at least one medical image systems of the plurality of medical image systems, one or more matched prior studies; retrieve, using the network device, image data corresponding to the matched current study and the one or more matched prior studies; generate an assembled study set comprising the matched current study, the one or more matched prior studies, the image data corresponding to the matched current study, and the image data corresponding to the one or more matched prior studies; process the assembled study set using the clinical application; and send, from the network device to the first image system, a processed study based on the assembled study set.

In at least one embodiment, the processor may be further configured to: receive, one or more additional series metadata corresponding to the current study; determine, based on a count of the one or more additional series metadata corresponding to the current study, that the current study is in progress.

In at least one embodiment, the first image series metadata may be pushed to the first server from at least one of the group of a PACS server, a Modality Worklist, and a medical image device; and wherein the at least one of the group of the PACS server, the Modality Worklist, and the medical image device may push the second image series metadata.

In at least one embodiment, the processor may be further configured to: send, from the first server to the first image system, one or more status queries corresponding to the current study; receive, from the first image system at the first server, one or more status responses corresponding to the one or more status queries; and determine, based on the one or more status responses, that the current study is in progress.

In at least one embodiment, the one or more status queries may comprise one or more polling requests; and the one or more polling requests may be sent from the first server to at least one of the group of a PACS server and a Modality Worklist; and the determining, based on one or more polling responses corresponding to the one or more polling requests, that the current study is in progress may be based on a change to the current study during a change threshold period of time.

In at least one embodiment, the one or more polling requests may be recurrently sent at a polling interval.

In at least one embodiment, the processor may be further configured to: determine, based on the polling response, that the current study has not changed at an expiry of the change threshold and that the current study is complete.

In at least one embodiment, the polling interval and the change threshold may be configurable.

In at least one embodiment, the polling interval and the polling threshold may be selected based on a performance metric of the first server.

In at least one embodiment, the processor may be further configured to determine that the matched current study is complete by: receive, at the first server, the second image series metadata; and apply, at the first server, one or more relevancy matching rules to the second image series metadata.

In at least one embodiment, the first image series metadata may correspond to a first series of medical images collected by the first image system; the second image series metadata may correspond to a second series of medical images collected by first image system; and the second image series metadata may be collected by the first image system after the first image series metadata is received at the first server.

In at least one embodiment, the processor may be further configured to: receiving, at the network device from the first image system in the plurality of medical image systems, third image series metadata corresponding to the matched current study.

BRIEF DESCRIPTION OF THE DRAWINGS

A preferred embodiment of the present invention will now be described in detail with reference to the drawings, in which:

FIG. 7B is an example of a matching rule of a clinical software application configuration.

FIG. 7C is an example configuration of a single study matching rule.

FIG. 7D is another an example configuration of a set of study matching rules.

FIG. 9B is a user interface showing an interface for changing a study matching rule.

FIG. 9C is a user interface showing an interface for changing a study matching rule enabling extended metadata field matching.

FIG. 9D is a user interface showing an interface for changing a series rule.

DESCRIPTION OF EXEMPLARY EMBODIMENTS

Figure 1A:
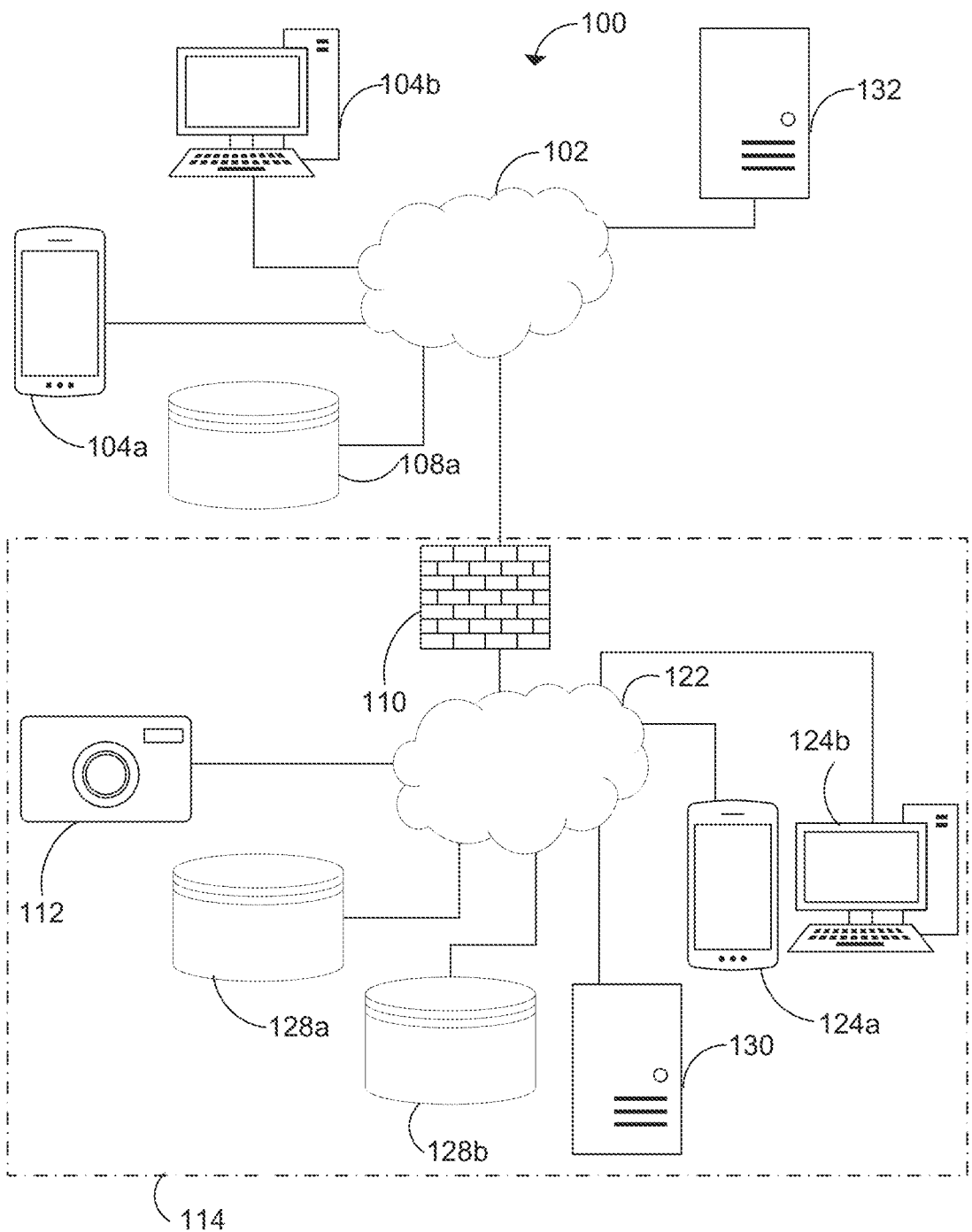
FIG. 1A is a system diagram of a medical organization including a medical data processing system.

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to below as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and a combination thereof.

Program code may be applied to input data to perform the functions described herein and to generate output information. The output information is applied to one or more output devices, in known fashion.

Each program may be implemented in a high level procedural, declarative, functional or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloads, magnetic and electronic storage media, digital and analog signals, and the like. The computer useable instructions may also be in various forms, including compiled and non-compiled code.

Various embodiments have been described herein by way of example only. Various modification and variations may be made to these example embodiments without departing from the spirit and scope of the invention, which is limited only by the appended claims. Also, in the various user interfaces illustrated in the figures, it will be understood that the illustrated user interface text and controls are provided as examples only and are not meant to be limiting. Other suitable user interface elements may be possible.

As described herein, "DICOM" refers to the Digital Imaging and Communications in Medicine (DICOM) standard for the communication and management of medical imaging information and related data as published by the National Electrical Manufacturers Association (NEMA).

As described herein, "HL7" refers to the Health Level 7 (HL7) standard as published by Health Level Seven International.

As described herein, "medical images", "image data", or "images" refers to image data collected by image acquisition devices, also known as "instances". The images are visual representations of the interior of a body anatomy that may be used for clinical analysis and medical interventions, commonly referred to as radiology. Radiology may use the imaging technologies including X-ray Plain Film (PF), digital X-rays, Cardiology imaging devices including a cardiology PACS server, Computed Tomography (CT) images, ultrasound images, nuclear medicine imaging including Positron-Emission Tomography (PET), Veterinary imaging devices, Magnetic Resonance Imaging (MRI) images, mammographic images, or any other standardized images used in a medical organization. Medical imaging also establishes a database of normal anatomy and physiology to make it possible to identify abnormalities. Medical imaging may further include removed organs and tissues. The medical images may be collected using analog means such as film and then subsequently scanned, or may be constructed from data originally collected using digital sensor means such as a Charge Coupled Device (CCD) and processed into image data. The image data may be provided in JPEG, JFIF, JPEG2000, Exif, GIF, BMP, PNG, PPM, PGM, PBM, PNM, WebP, HDR, HEIF, or any other known format. The image data may be provided in an uncompressed image format, in a lossless compressed format, or in a lossy compressed format.

While existing data processing systems generally provide non-contextual processing, and do not determine the relevancy of one study to another for processing, the processing of the clinical software applications herein includes information enhancement that are only relevant to specific types of data, perform more efficiently with specific, relevant data, and indeed the processing may not function properly at all without such specific relevant data.

The clinical software applications of the medical image processing system may provide clinically relevant information, such as by adding new medical images and image metadata. This information enhancement may include adding metadata fields, manipulating images, and associating a plurality of studies, series, and image data and metadata together from disparate sources.

As described herein, clinical software applications are software applications that generate additional information about a medical study or studies through the analysis of metadata and/or the image data including pixel data of one or more images of the study or studies. Such analysis might range from simple to highly complex calculations including statistical inferences and machine learning. The analysis by the clinical software application may be "global" in the sense that it takes account of pixels and/or meta-data across an entire matched set of images, or several sets of images. The clinical software application analysis may add clinically relevant information as described herein. Alternatively, the analysis may be a "local" analysis that, e.g. only performs determinations based on a single image or fragment of meta-data. Further, the clinical software application may add information, including probabilistic information such as confidence levels, probabilities, and/or certainties, in addition to just performing a transformation of the data (for example, the transformation may go beyond simple image compression). The decision making and rule application for each clinical software application can be used for making "routing" decisions for determining the relevancy of a set of images to a particular clinical software application.

Specific examples of clinical software applications may include (but are not limited to): image registration, anatomy recognition, contrast detection, image quality, quantification of brain abnormalities and changes from MR images in order to track disease evolution, liver iron concentration analysis from MR images of the liver, and the removal of personally identifying information.

Reference is first made to FIG. 1A, which illustrates a medical data processing system 100. The system 100 has a plurality of user devices 104 (including mobile device 104a and computer device 104b), network 102, a remote server 132, and a remote enterprise imaging device 108a. The system 100 further comprises a medical organization 114 including a medical organization network 122 that is connected to network 102 by firewall 110. Within the medical organization network 122, there is a plurality of medical organization user devices 124 (including mobile device 124a and computer device 124b) that are generally the same type of devices as those in the plurality of user devices 104. The medical organization network 122 also has a processing server 130, one or more enterprise imaging devices 128a and 128b, and one or more image acquisition devices 112.

In an alternate embodiment, the processing server 130 may be external to the medical organization 114 and the enterprise imaging devices 128 may forward image data and associated metadata to the external processing server via network 122, firewall 110, and network 102.

User devices 104 and medical organization user devices 124 may be used by end users to access an application (not shown) running on remote server 132 over network 102 and network 122. For example, the application may be a web application, or a client/server application. The user devices 104 and medical user devices 124 may be desktop computers, mobile devices, or laptop computers. The user devices 104 and medical user devices 124 may display the web application, and may allow a user to review medical data, including medical images and image metadata, from medical organization 114. The users at user devices 104 and medical organization devices 124 may be a clinician user at medical organization 114 who may review the medical data, including processed medical data from the clinical software applications. A clinician user may be a radiologist whose role is the review (or reading) of medical images, or a referring clinician (for example, the non-radiologist clinician who referred the patient for a scan) who may receive a report from the radiologist.

The users at user devices 104 and medical organization devices 124 may be an administrator user who may administer the configuration of clinical software applications or matching rules for medical organization 114.

Enterprise imaging devices may include both remote enterprise imaging device 108a, first enterprise imaging device 128a inside the medical organization 114, and second enterprise imaging device 128b inside the medical organization 114. While a single remote enterprise imaging device 108a is shown, it is understood that there may be a plurality of remote enterprise imaging devices. Similarly, while only two enterprise imaging device 128a and 128b are shown, it is understood that there may be more enterprise imaging devices.

The enterprise imaging devices may be a Picture Archiving and Communication System (PACS) server, a Modality Worklist (MWL), a medical image data archive or another enterprise imaging device. For example, an enterprise imaging device may be an IntelePACS® from Intelerad®, an IntelliSpace® PACS from Philips®, an enterprise imaging device such as the Enterprise Imaging Solution® suite from Change Healthcare®. For example, an enterprise imaging device may be a Medicor® MiPACS® Modality Worklist. For example, an enterprise imaging device may be an IBM iConnect Enterprise Archive.

Remote enterprise imaging device 108a may be located remotely from the medical organization 114. There may be one or more remote enterprise imaging devices 108a. For example, a remote PACS may be at an affiliated medical organization to the medical organization 114, for example, a satellite clinic. A remote enterprise imaging device 108a may provide economical storage and convenient access to medical images and image metadata from multiple image acquisition devices external to medical organization 114. A PACS may support live Query/Retrieve, archive Query/Retrieve, be configured to auto-forward, or a combination of these roles.

Remote enterprise imaging device 108a may be a Modality Worklist (MWL), where the MWL makes patient demographic information from a Radiology Information System (RIS) available at an image acquisition device, and providing, amongst other things, a worklist of patients who will attend the image acquisition device for imaging in the near future. The MWL may further provide in-progress studies and completed studies.

Remote enterprise imaging device 108a may be a remote imaging image acquisition device configured using auto-forward to the medical organization 114.

The remote enterprise imaging device 108a may store image metadata in a DICOM format, an HL7 format, an XML-based format, or any other format for exchanging image data and associated metadata.

Remote server 132 may be a commercial off-the-shelf server. In an alternate embodiment, the remote server 132 may be a server running on Amazon® Web Services (AWS®) or another similar hosting service. The remote server 132 may be a physical server, or may be a virtual server running on a shared host. The remote server 132 may have an application server, a web server, a database server, or a combination thereof. The application server may be one such as Apache Tomcat, etc. as is known. The web server may be a web server for static web assets, such as Apache® HTTP Server, etc. as is known. The database server may store user information including structured data sets, electronic form mappings, and other electronic form information. The database server may be a Structured Query Language (SQL) such as PostgreSQL® or MySQL® or a not only SQL (NoSQL) database such as MongoDB®.

The remote server 132 is in communication with processing server 130, and may provide data analysis for the processing server, or data aggregation in conjunction with processing server 130. The remote server 132 may provide a web-based interface for browsing analysis of the medical data and the clinical software applications running at processing server 130.

In an alternate embodiment, the remote server 132 may be provided inside the medical organization 114 and connected to the processing server 130 via network 122.

In another alternate embodiment, there may be more than one server providing the functionality of remote server 132, including one inside the medical organization 114 in communication with processing server 130 via network 122, and a second remote server accessible to the medical organization 114 via network 122, firewall 110, and network 102.

Network 102 may be a communication network such as the Internet, a Wide-Area Network (WAN), a Local-Area Network (LAN), or another type of network. Network 102 may include a point-to-point connection, or another communications connection between two nodes.

Network 122 may be a communication network such as an enterprise intranet, a Wide-Area Network (WAN), a Local-Area Network (LAN), or another type of network. Network 122 may include a point-to-point connection, or another communications connection between two nodes. The Network 122 may exist at a single geographical location, or may span multiple geographical locations. Network 122 is separated from network 102 by firewall 110, which may provide for Network Address Translation for the medical organization 114, Virtual Private Network access for the remote user devices 104, Access Control Lists for network traffic sent between network 122 and network 102 (and vice-versa).

Firewall 110 may be a commercial off-the-shelf network firewall that performs network translation and routing between network 102 and network 122. For example, firewall 110 may be a Cisco® firewall, a Sonicwall® firewall, or another firewall as is known.

Medical organization 114 may include one or more related medical organizations that share medical image data and associated metadata over one or more networks. The one or more related medical organizations may include one or more image acquisition devices, one or more geographical locations, a plurality of clinician users, a plurality of administrative users, and a plurality of patients attending the one or more image acquisition devices for medical imaging services.

The medical organization 114 has a firewall 110, one or more image acquisition devices 112, a first enterprise imaging device 128a, a second enterprise imaging device 128b, a processing server 130, one or more medical user devices 124 such as mobile device 124a and computer device 124b, and medical network 122.

The one or more image acquisition devices 112 may be a variety of different imaging modalities that generate medical images such as X-ray Plain Film (PF) devices, digital X-ray devices, Computed Tomography (CT) devices, ultrasound devices, nuclear medicine imaging devices including Positron-Emission Tomography (PET) devices, Magnetic Resonance Imaging (MRI) devices, mammographic devices, or any other imaging modality used in a medical organization. The one or more image acquisition devices 112 may be mobile imaging devices such as mobile CT scanners. The medical images generated by the one or more imaging devices may be collected using analog means such as film and then subsequently scanned, or may initially be collected using digital sensor means such as a Charge Coupled Device (CCD). The one or more image acquisition devices 112 may operate to produce studies of patients of the medical organization 114. The one or more image acquisition devices 112 may collect various metadata at the time it captures images of the patient. The metadata collected by the one or more image acquisition devices 112 may be in DICOM format, HL7 format, or other formats for image data and associated metadata formats as are known. The one or more image acquisition devices 112 may include, for example, a General Electric® (GE®) Revolution Apex® CT image acquisition device, a Siemens® Magnetom Vida® MR image acquisition device, and a Canon® UltiMax® x-ray image acquisition device.

The first enterprise imaging device 128a and the second enterprise imaging device 128b may be PACS. In an alternate embodiment, either the first or the second enterprise imaging devices 128 may be a Modality Worklist at one of the one or more image acquisition devices 112. The enterprise imaging device 128 may store medical image data collected at the one or more image acquisition devices 112, and image metadata corresponding to the medical image data.

The image data generated by the one or more image acquisition devices 112 and stored in the first enterprise imaging device 128a and second enterprise imaging device 128b may be provided in JPEG, lossless JPEG, Run-Length Encoding (RLE), JFIF, JPEG2000, Exif, GIF, BMP, PNG, PPM, PGM, PBM, PNM, WebP, HDR, HEIF, or any other known image format.

Processing server 130 may be a commercial off-the-shelf server system. The processing server 130 may be configured to execute a software platform that manages the processing of medical images, and further executes one or more clinical software applications to process the medical images, as discussed herein. The processing server 130 may be a physical server, or may be a virtual server running on a shared host. The processing server 130 can be a single server, or multiple different individual servers configured to work cooperatively to provide the platform application and the one or more clinical software applications. The processing server 130 is connected via network 122 to the enterprise imaging devices 128, the one or more image acquisition devices 112, and medical user devices 124. The processing server 130 is further in network communication with the remote enterprise imaging device 108a and remote server 132 via network 122, firewall 110, and network 102.

Figure 1B:
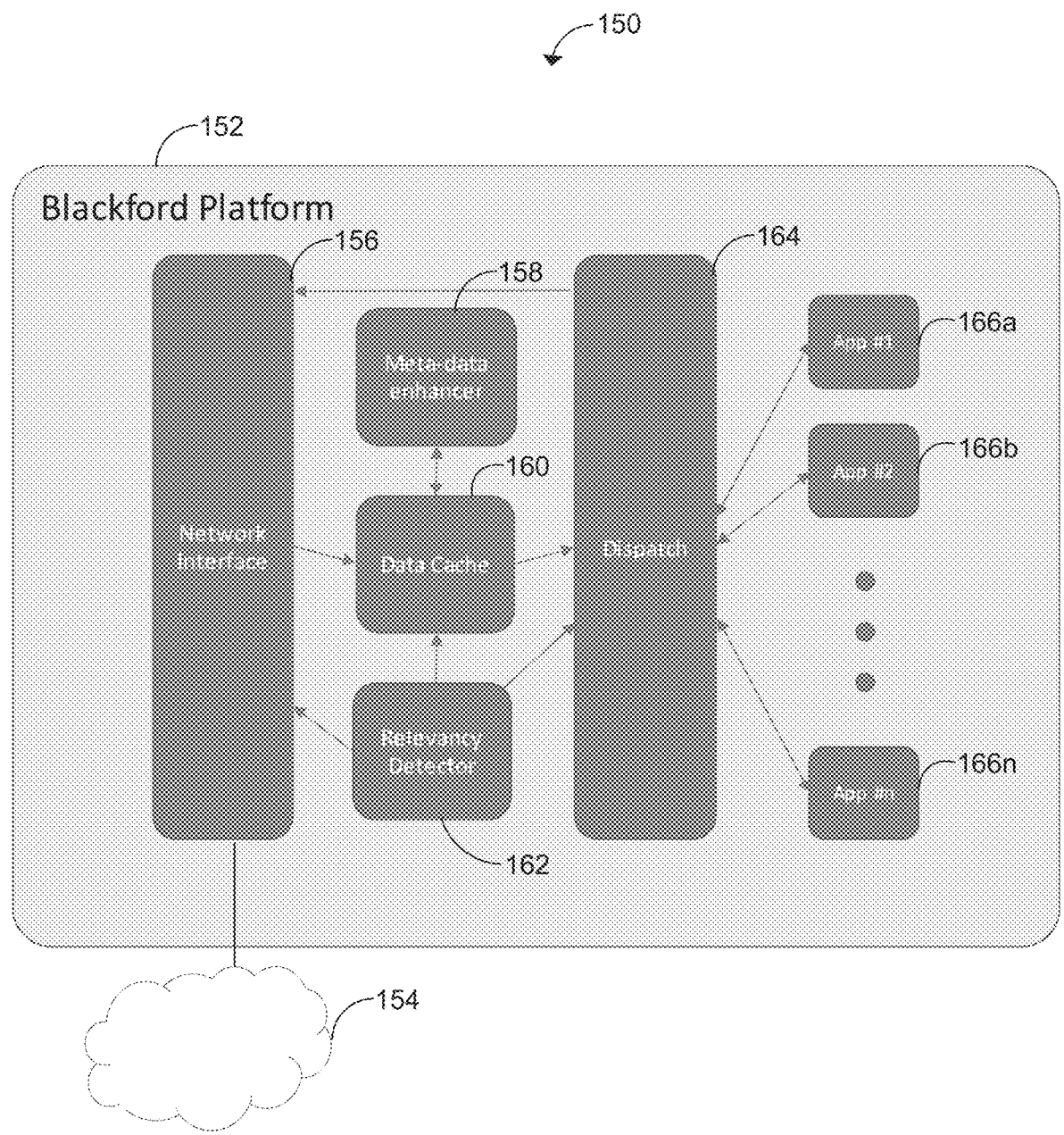
FIG. 1B is a block diagram of the medical data processing system from FIG. 1A.

Reference is next made to FIG. 1B, showing a block diagram 150 of the medical data processing system 130 from FIG. 1A. The processing system 152 may be a platform for processing medical images and image metadata, including a network interface 156 in communication with network 154, a meta-data enhancer 158, a data cache 160, a relevancy detector 162, a dispatcher 164, and one or more clinical software applications 166.

The processing system 152 receives medical image data and associated image metadata from devices on network 154 using network interface 156. The network interface 156 connects the processing server to the medical organization networks using a variety of protocols and modes of operation. The network interface 156 may receive medical image data and associated image metadata using a push mode of operation, where image devices send data to the processing server. In an alternate embodiment, the network interface 156 may send a polling request to one or more image devices using a "pull" mode of operation of the medical image data and associated metadata. In another alternate embodiment, the network interface 156 receives medical images and image metadata using both a pull and a push mode of operation from the image devices.

The metadata enhancer 158 serves to enhance the image metadata in the data cache 160 by adding new metadata that may be determined by analysis of the original image and/or associated image metadata. In an alternate embodiment, the metadata enhancer 158 may enhance image metadata by adding new metadata that may be determined by analysis of pixel data in the data cache 160.

The data cache 160 of the processing system 152 is a software component for assembling received image data. The data cache 160 may have two distinct caches, a first cache for image data and a second cache for metadata associated with the image data. The data cache 160 may store image data and/or associated metadata based upon a first query response, and may provide a locally cached copy of the image data and/or associated metadata to the components of the platform 152 upon a second query. In this manner, the data cache 160 may provide image data and associated metadata to the components of the platform 152 without the need for a query request to be sent using network interface 156 and network 154. The data cache 160 may buffer incoming studies and may allow for incoming studies (and images associated with studies) to arrive at different times. To address the situation where partial data is received for an incoming study, the data cache 160 may hold a study pending arrival of the rest of the data for that study.

The data cache 160 of the processing system 152 may be an off-the-shelf caching program such as memcached, redis, or another caching application as is known. The data cache 160 of the processing system 152 may be a proprietary caching solution.

The data cache 160 may also provide for read through and lazy loading functionality such that data is only loaded into the data cache 160 as needed, and upon request of other components of the processing system 152.

The data cache 160 may cache both the medical images and the image metadata. As well as caching data until all relevant data is available for an application, the data cache 160 may also cache data so that any study, series or image data may be only fetched once over the network within a time interval, even though it may be used by several different clinical software applications.

The relevancy detector 162 determines if a received study matches one or more of the clinical software applications 166 based on one or more relevancy matching rules associated with the configuration of each clinical software application. The relevancy detector 162 may further determine that, based on the relevancy rules for a particular clinical software application, that additional queries should be made to determine the existence of one or more matching prior studies, and/or one or more matching prior series. The determination for further queries to locate prior studies or prior series may be made based on a rule configuration. To locate the matching prior studies and series, the relevancy detector may send queries using network interface 156 to one or more enterprise imaging devices.

The dispatcher 164 determines an assembled study set based on the received query response data from the relevancy detector 162 and/or the data cache 160. The dispatcher 164 may receive study data, image data, series data, and metadata from the query response or from the data cache 160. The dispatcher 164 may determine the assembled data set based on relevant data and is responsible for loading, notifying, or executing any clinical software applications 166 matching the current study based on the rules configured in the clinical software application configuration. Any matching clinical software applications 166 may then be executed to process the assembled data set. The dispatcher 164 may further send the processing result of a clinical software application using network interface 156, so that it may be sent to one or more enterprise imaging devices. The processing result may include new medical images, or new image metadata, and the processing result may be associated with the studies, series, and images associated with the assembled data set.

The one or more clinical software applications 166 provide data processing capabilities to the assembled result set. One example of a clinical software application is image registration, where a matching set of medical data is associated together in a new metadata object, however, other clinical software applications are contemplated too. Clinical software applications that process medical data automatically may themselves create processed data and other medical data, including medical images and metadata.

In one example, a clinical software application 166 may be a registration application. The registration application performs an analysis of the metadata or pixel data in the images of two series, for instance, two scans at different times of a spatially overlapping area of the same patient. The registration application may analyze two series from the same study or two series from different studies. The registration application may then infer a spatial relationship between the two scans, i.e. a geometrical transformation that aligns one set of images with the other, which is then recorded as new metadata associated with the images. The registration clinical software application may be both a processing end in its own right, e.g. it allows end users to avoid having to manually align scans when they view them, but also potentially a method of generating additional metadata in order to determine how to route the study data to another clinical software application 166.

In another example, a clinical software application 166 may be anatomy recognition. The anatomy recognition application performs an analysis of the pixel data in the images of a study and probabilistically determines the area of anatomy that is likely the subject of the scan. This information can be used instead of other lower confidence metadata that is associated with the studies, or in conjunction to lower confidence metadata to arrive at a higher confidence prediction about the identified anatomical part. This clinical software application may also be used to provide a more refined determination of anatomy than the original metadata alone can provide, i.e. sub-sections of an anatomical part.

In another example, a clinical software application 166 may be contrast detection. The contrast detection application performs an analysis of the pixel data in the images of a study, determines whether the scan was done with a contrast agent or not, and then adds supplemental image metadata to the image or study identifying that a contrast agent was used during the collection of the image. As above, the contrast detection application could be used to supplement or replace existing image metadata already available with the study or images. In cases such as this, a series of images may be captured in the study in a shorter time frame, and these would be in the same study. The contrast detection may include the detection of which particular contrast agent was used.

In another example, a clinical software application 166 may be an image quality application. The image quality application performs an analysis of the pixel data in the images of a study, determines whether the scan is of sufficient quality (e.g., low noise levels, contrast, etc.) for use in further processing by the clinical software applications.

In another example, a clinical software application 166 may be a Personal Health Information (PHI) Removal application. In the PHI Removal application, pixel data may be analyzed to detect presence of identifying information in the images themselves (e.g., a patient name "burnt into" the image). The PHI Removal application may create a new set of images with the PHI data removed if, for example, the images were intended for storage off-site.

In another example, a clinical software application 166 may be a quantification application of brain abnormalities and changes between studies. The clinical software application 166 may quantify and objectively track clinically identified portions of studies, including image data and associated metadata. Such an application may, for example, track the evolution of multiple-sclerosis in a patient.

In another example, a clinical software application 166 may provide an estimate of liver-iron-concentration from a study of the liver.

Figure 2:
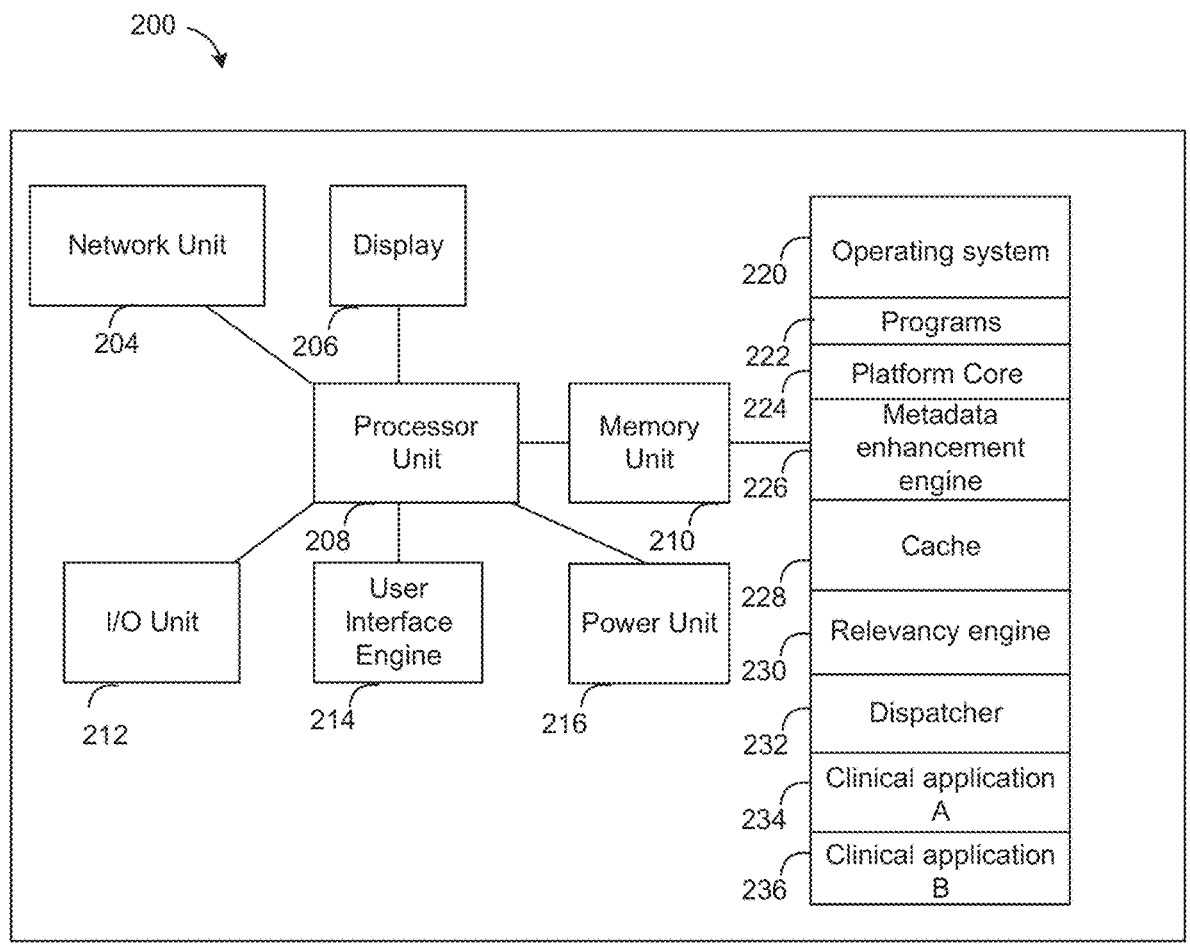
FIG. 2 is a block diagram of the processing server 130 from FIG. 1A.

Reference is next made to FIG. 2, showing a block diagram 200 of the processing server 130 from FIG. 1A. The processing server 200 has network unit 204, display 206, I/O unit 212, processor unit 208, memory unit 210, user interface engine 214, and power unit 216. The memory unit 210 has operating system 220, programs 222, a platform core 224, a metadata enhancement engine 226, a cache 228, a relevancy engine 230, a dispatcher 232, a clinical software application A 234 and a clinical software application B 236. The processing server 200 may be a virtual server on a shared host, or may itself be a physical server.

The network unit 204 may be a standard network adapter such as an Ethernet or 802.11x adapter. The processor unit 208 may include a standard processor, such as the Intel Xeon processor, for example. Alternatively, there may be a plurality of processors that are used by the processor unit 208 and may function in parallel. Alternatively there may be a plurality of processors including a Central Processing Unit (CPU) and a Graphics Processing Unit (GPU). The GPU may be, for example, from the GeForce® family of GPUs from Nvidia®, or the Radeon® family of GPUs from AMD®. There may be a plurality of CPUs and a plurality of GPUs.

The processor unit 208 can also execute a user interface engine 214 that is used to generate various GUIs, some examples of which are shown and described herein, such as in FIGS. 9A, 9B, 9C, and 9D. The user interface engine 214 provides for clinical software application configuration layouts for users to configure clinical software applications, rule configuration layouts for users to configure relevancy matching rules, and the information submitted using these interfaces may be processed by the relevancy engine 230, clinical software application A 234 and/or clinical software application B 236. User interface engine 214 may be an Application Programming Interface (API) or a Web-based application that is accessible via the network unit 204.

I/O unit 212 provides access to server devices including disks and peripherals. The I/O hardware provides local storage access to the programs running on processing server 200.

The power unit 216 provides power to the processing server 200.

Memory unit 210 may have an operating system 220, programs 222, a platform core 224, a metadata enhancement engine 226, a cache 228, a relevancy engine 230, a dispatcher 232, a clinical software application A 234, and a clinical software application B 236.

The operating system 220 may be a Microsoft Windows Server operating system, or a Linux-based operating system, or another operating system.

The programs 222 comprise program code that, when executed, configures the processor unit 208 to operate in a particular manner to implement various functions and tools for the processing server 200.

The platform core 224 provides functionality for managing the processing server 200. This may include providing an API available via the network unit 204 for administration of the processing server, including configuration of the clinical software application A 234, clinical software application B 236, and relevancy engine 230. Alternatively, a user may access a web interface of the platform core 224 via the user interface engine 214 and/or the network unit 204 to administer the processing server 200.

The platform core 224 may be deployed to a physical server or a virtual server on the same network as its host medical organization. In one embodiment, the platform core 224 may be deployed as a Windows® Service.

The platform core 224 may include a settings editor that allows an administrator to configure the platform core 224, or other components.

The platform core 224 may report anonymized telemetry data to the remote server (see FIG. 1A at 132).

The metadata enhancement engine 226 may analyze incoming studies and images to generate supplementary image metadata. The supplementary image metadata may be generated as a metadata object and sent to the enterprise imaging devices, where it may be stored in association with the current study. In an alternate embodiment, the metadata enhancement engine 226 may receive processed studies from the dispatcher 232, and may generate metadata objects corresponding to the processed studies and/or processed images. The generated metadata objects may be stored in the one or more enterprise imaging devices in association with the current study.

The cache 228 is cache for assembled study sets. The cache may be stored in memory 210, or stored in memory 210 and on a storage device attached at I/O Unit 212. The cache 228 includes a storage portion in memory where medical images, image metadata, study data, study metadata, series data, and series metadata may be stored as the processing server is generating the assembled matched study set for processing at the clinical software applications (e.g. clinical software application A 234). Study data, study metadata, series data, series metadata, image data, and image metadata may be received at the processing server 200 at network unit 204, and then stored in cache 228.

The relevancy engine 230 receives study metadata, series metadata, and image metadata, along with images corresponding to the study metadata, images corresponding to the series metadata, and images corresponding to the image metadata. Study metadata may refer to series metadata and image metadata. The relevancy engine 230 has access to a superset of relevancy matching rules. Each of the relevancy matching rules may be independently configured as described in FIGS. 7A, 7B, 7D, 9A, 9B, and 9C. Each relevancy matching rule may identify corresponding metadata matching patterns for a first study that may direct the relevancy engine 230 to identify and associate the first study with a second study. Similarly, relevancy matching rules may identify corresponding metadata matching patterns for a series that may direct the relevancy engine 230 to identify the series as being related to a study.

Similarly, relevancy matching rules may identify corresponding metadata matching patterns for a prior study that may direct the relevancy engine 230 to identify the prior study as being related to a current study.

Dispatcher 232 dispatches the assembled matched study set to the one or more clinical software applications (for example, clinical software application A 234 and clinical software application B 236). This may involve an inter-process communication, or a network communication using network unit 204. Once processing is completed, the dispatcher may receive a processed study based on the assembled matched study set and may send the processed study to one or more image devices in the plurality of image devices (for example, enterprise imaging device 128*a*, enterprise imaging device 128*b* in FIG. 1A) using network unit 204.

Each of clinical software application A 234 and clinical software application B 236 is a software application that accepts the assembled matched study set and performs some processing (as described at FIG. 2) and then generates a processed study that is sent to the dispatcher 232. While only two clinical software applications are shown in FIG. 2, it is understood that there may be any number of clinical software applications, and potentially many more clinical software applications.

The clinical software applications may run in a process at processing server 200. In an alternate embodiment, the clinical software applications may run in a virtual machine (e.g. using VMware ESX) or a container (e.g. using Docker) at processing server 200. In another alternate embodiment, the clinical software applications may be located separately from processing server 200 in network communication with processing server 200, and in such a case the dispatcher 232 may transmit the assembled matched study set to the clinical software application using network unit 204, and receive the processed study back from the clinical software application using network unit 204. In another alternate embodiment, a combination of clinical software application hosting may be used, for example a first clinical software application in one or more clinical software applications may run in a process at a processing server 200, a second clinical software application in the one or more clinical software applications may be located separately from the processing server 200, and a third clinical software application in the one or more clinical software applications may be located in a virtual machine or container at processing server 200.

In an alternate embodiment, the clinical software applications may be software modules provided via a remote cloud-hosted service which are accessed by using a remote API.

Figure 3A:
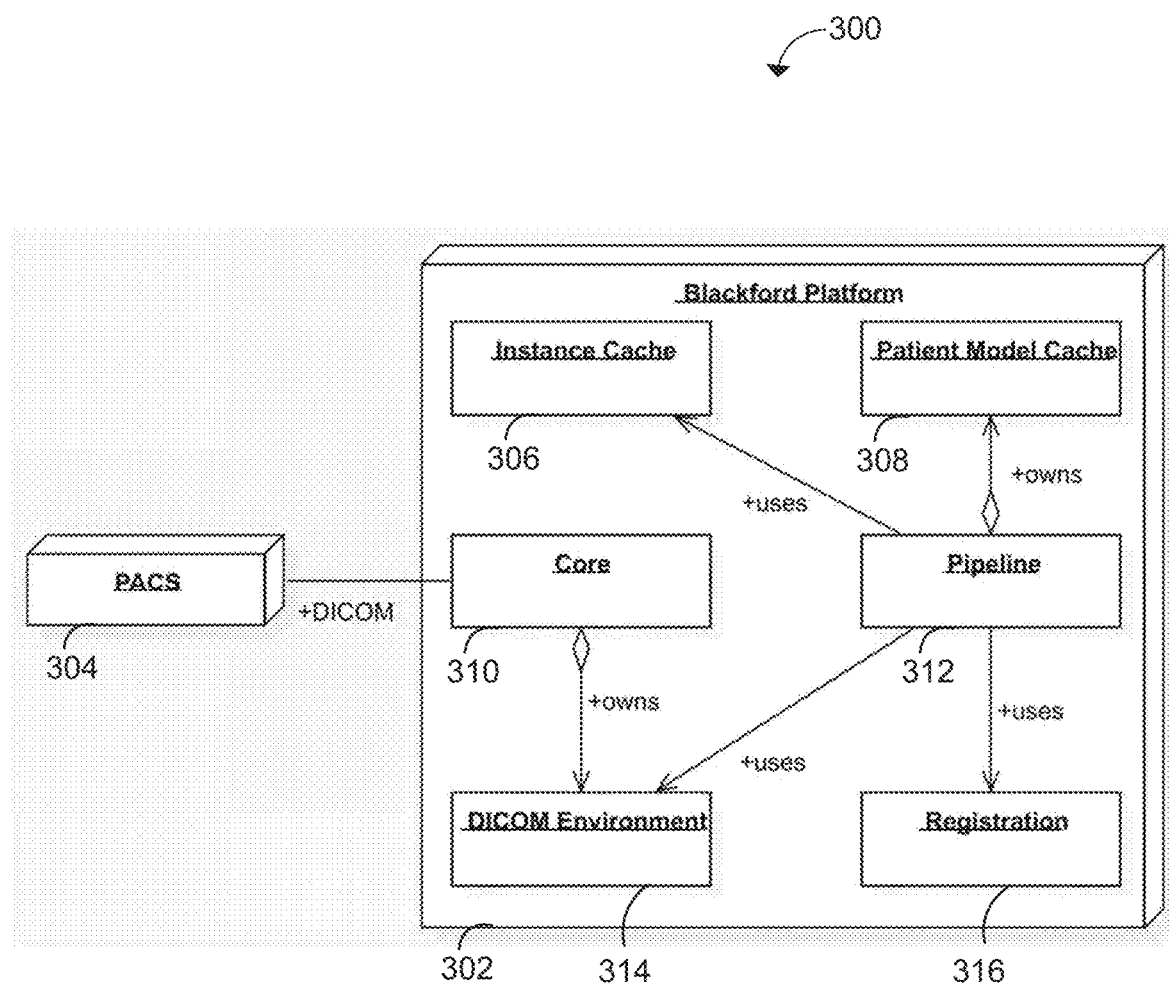
FIG. 3A is a software component diagram of the medical data processing system from FIG. 1A.

Referring to FIG. 3A, there is shown a software component diagram 300 of the platform 302.

The platform 302 receives metadata, including study metadata, series metadata, and image metadata from an enterprise imaging device 304. The metadata may be in a format such as the DICOM format or the HL7 format. The enterprise imaging device 304 may be a PACS server, or a Modality Worklist server.

The platform 302 has an instance cache 306, a patient model cache 308 (which may be part of data cache 160 in FIG. 1B), a core 310, a pipeline 312, a metadata environment 314, and a registration module 316. For example, in the case where the metadata environment is the DICOM format, the core 310 may make a set of configured DICOM application entities known to the Pipeline as the DICOM Environment 314. These DICOM application entities may serve to provide a common API for the enterprise imaging device 304, represented as a PACS server for the purposes of this example, and the Pipeline 312 to communicate.

The metadata environment 314 may be configured to use any medical data standard designed to provide for the processing of medical images, or to use non-standard or proprietary communication protocols for the processing of medical images.

For example, the metadata environment 314 may be a DICOM environment that implements the DICOM standard, where the pipeline 312 may examine the DICOM Environment 314 to determine and retrieve relevant current and prior studies as they are received. The pipeline 312 may further dispatch DICOM images for registration at registration module 316.

The patient model cache 308 may record and cache patients, studies and series as they are processed at the pipeline 312.

The instance cache 306 may cache known DICOM images.

The registration module 316 may register common frames of reference encoded in supplied DICOM images. This common frame of reference may be a DICOM entity associated with each of the DICOM images that provide the common frame of reference. The DICOM frame of reference may ensure the spatial relationship of images within a series, and may allow images across multiple series to share the same frame of reference. The frame of reference may be a coordinate system, and may be constant for all images related to a specific frame of reference. The registration module 316 may be a clinical software application running on the platform 302 (see e.g. clinical software applications 166 in FIG. 1B, and clinical software application 234 and clinical software application 236 in FIG. 2).

Figure 3B:
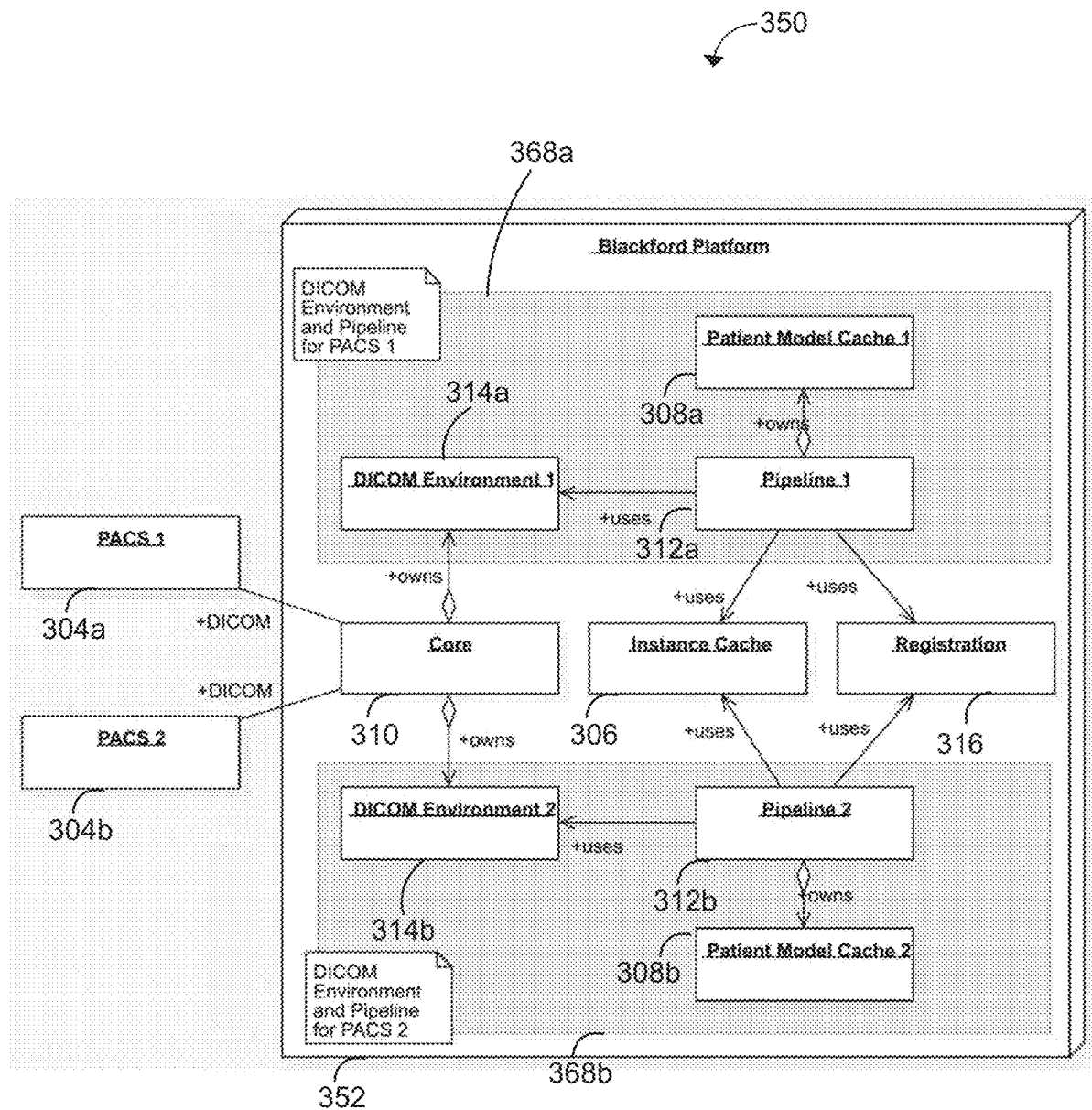
FIG. 3B is an alternate embodiment of a software component diagram 350 of the medical data processing system from FIG. 1A.

Referring to FIG. 3B, there this is shown a software component diagram 350 of an alternate embodiment of the platform 352. In FIG. 3B, like numbers represent like components from FIG. 3A.

The platform 352 shows an alternate embodiment of the platform 302 in FIG. 3A. For more complex deployments, multiple Platform instances can be used to process studies, for example, first platform 368*a* and a second platform 368*b*. The first platform 368*a* and the second platform 368*b* may also share components, including the core 310, the instance cache 306, and a registration module 316. In the alternate configuration 352, the first platform 368*a* and the second platform 368*b* may each process a distinct subset of studies.

This alternate configuration 352 can include processing of medical image data by multiple enterprise imaging devices, for example, the first enterprise imaging device 304*a* and the second enterprise imaging device 304*b*. In this example, a different metadata environment 314 is used for each enterprise imaging device. For Example, DICOM environment 314*a* may be used for PACS server 1 304*a*, and DICOM environment 314*b* may be used for PACS server 2 304*b*. In this example, studies discovered within a given DICOM environment 314 are processed by multiple dedicated pipelines 312.

In an alternate embodiment of either 3A or 3B, multiple platform instances may be used to process medical data in parallel, for example, in the case of high volume platform deployments, or in situations where high availability of the platform is important.

Figure 4A:
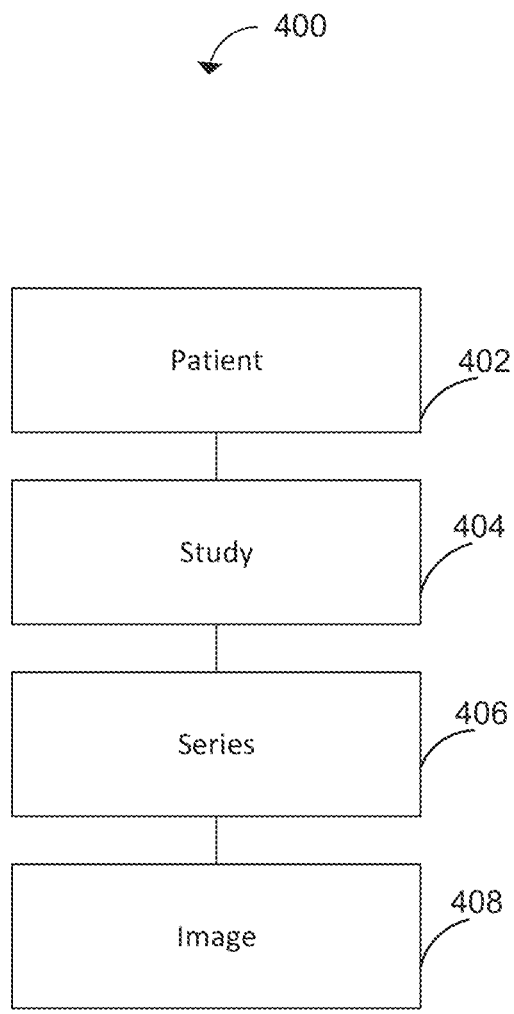
FIG. 4A is a block diagram of a metadata object model.

Referring next to FIG. 4A, there is shown a block diagram 400 of a metadata object model. The metadata object model has patient entities 402, study entities 404, series entities 406, and image entities 408. The metadata object model may be normalized. The metadata object model may be used in association with a database at the processing server, a cache at the processing server, or another storage medium at the processing server to provide a relational database to store the incoming metadata.

Each of the patient entity 402, study entity 404, series entity 406 and image entity 408 may be composite entities that comprise other entities, other fields, or any other individual metadata fields as required.

A patient entity 402 may have a plurality of associated studies 404. A study may have a plurality of associated series 406. A series may have a plurality of associated images 408.

A patient entity 402 may have a plurality of metadata elements associated with it, including (but not limited to) the patient's name, a patient identifier, a patient's birth date, a patient's sex, and comments associated with the patient. The plurality of metadata elements in the patient entity 402 may have a user-entered source, a MWL source, or a combination thereof.

A study entity 404 may have a plurality of metadata elements associated with it, including (but not limited to) study instance identifier (or UID), a study date, a study time, a referring physician's name, a study identifier, an accession number, a study description, a referenced study sequence, a referenced SOP class identifier (or UID), and a reference SOP instance identifier (or UID). Other study metadata may include an admitting diagnosis description, a patient age, and a patient weight. The plurality of metadata elements in the study entity 404 may have a user-entered source, an automated source (for example, the date and time of a study may be automatically populated by an enterprise imaging device when the study is collected), a MWL source, or a combination thereof.

A series entity 406 may have a plurality of metadata elements associated with it, including (but not limited to) modality, series instance UID, series number, series date, series time, performing physician's name, protocol name, series description, operator's name, referenced performed procedure step sequence, referenced SOP class UID, referenced SOP instance UID, request attributes sequence, requested procedure ID, scheduled procedure step ID, scheduled procedure step description, scheduled protocol code sequence, performed procedure step ID, performed procedure step start date, performed procedure step start time, performed procedure step description, performed protocol code sequence, and comments on the performed procedure step. The plurality of metadata elements in the series entity 406 may have a user-entered source, an automated source (for example, the date and time of a series may be automatically populated by an enterprise imaging device when the study is collected), a modality performed procedure step, a MWL source, or a combination thereof.

An image entity 408 may alternatively be referred to as a DICOM Service Object Pair (SOP) Instance. The SOP Instance is used to reference both image and non-image DICOM instances. The image entity 408 may have a plurality of metadata elements associated with it, including (but not limited to) manufacturer, institution name, station name, manufacturer's model name, device serial number, software version, private creator, equipment UID, and service UID. An image entity 408 may further have metadata including an application header sequence, an application header type, an application header ID, an application header version, workflow control flags, and archive management flags. There may further be modality (or image acquisition device) specific metadata in the image entity 408. The plurality of metadata elements in the image entity 408 may have an automated source (for example, the date and time of an image may be automatically populated by an enterprise imaging device when the study is collected), configuration based sources, or a combination thereof.

An entity may have a unique identifier. In the example of DICOM metadata, there may be a Unique Identifier, and the Unique Identifier may be globally unique across the entire DICOM environment.

Figure 4B:
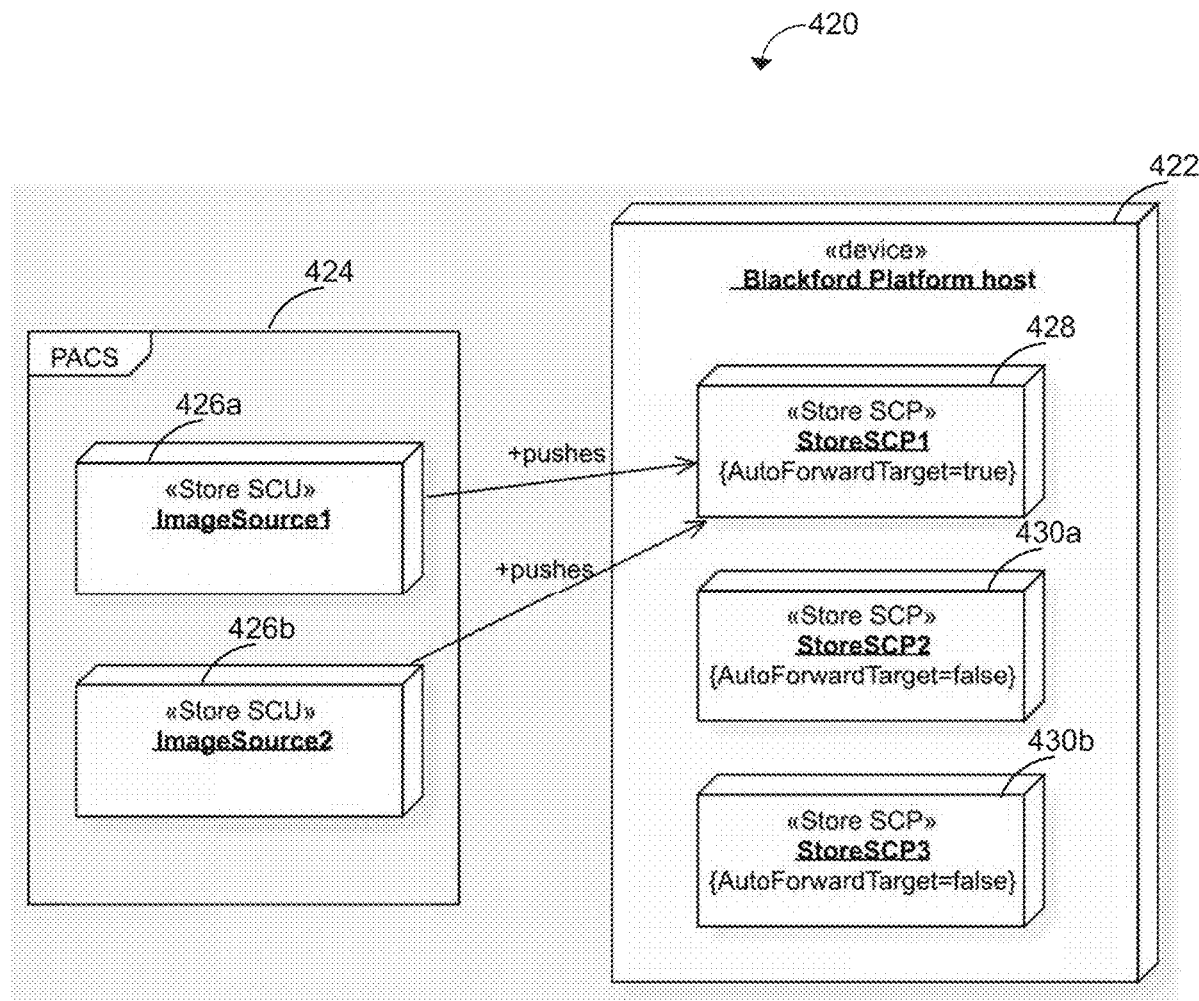
FIG. 4B is a dataflow diagram of a platform that uses auto-forwarding for discovery of current studies.

Referring next to FIG. 4B, there is shown a dataflow diagram 420 of a platform 422 that configured to allow new studies to be pushed to it. The platform 422 runs on a processing server (see 130 in FIG. 1A), and may have one or more interfaces 428, 430*a* and 430*b* capable of sending and receiving image data and associated metadata communicated over a network device for interaction with other enterprise imaging devices. The enterprise imaging device 424 may have one or more data sources, such as a first data source 426*a* and a second data source 426*b*, the data sources capable of sending and receiving image data and associated metadata communicated over a network device for interaction with the platform 422. In FIG. 4B the data sources may be configured to automatically forward (auto-forward) certain studies to the platform. In other embodiments transfer of a study from a data source may be initiated manually, or via some other mechanism. It is understood that the data sources 426 and the interfaces 428 and 430 may use any suitable data exchange format.

In an example implemented using the DICOM standard for exchange of imaging data and associated metadata, the platform 422 includes three DICOM connection points providing the DICOM storage service::first Store-SCP 428, second Store SCP 430*a*, and third Store SCP 430*b*.

A DICOM "SCU" refers to a client role (Service Class User). A DICOM "SCP" refers to a server role (Service Class Provider). A Storage-SCP may offer an interface for persistently storing studies and image data in a DICOM-compliant manner. A Storage-SCU may offer an interface to send studies in a DICOM-compliant manner.

In the example shown in FIG. 4B, a first Store-SCP 428, a second Store SCP 430*a*, and a third Store SCP 430*b* may be separate DICOM interfaces that implement a DICOM compliant storage SCP interface, i.e. three separate interfaces are provided for storing data. The first Store-SCU box 426*a* and second Store-SCU box 426*b* may be separate software instances or processes that implement a DICOM compliant interface that may transmit data to a storage-SCP (such as the first Store SCP 428, the second Store SCP 430*a*, and the third Store SCP 430*b*) for storage.

The first Store SCU 426*a* and the second Store SCU 426*b* may have outgoing network ports capable of transmitting DICOM formatted image data and metadata.

The first Store SCP 428, the second Store SCP 430*a*, and the third Store SCP 430*b* may have incoming network ports capable of receiving DICOM formatted image data and metadata.

The platform 422 may have many different configurations of Store SCP targets, different flags such as the auto-forward flags of the enterprise imaging device 424. As shown in the DICOM embodiment in FIG. 4B, the Store SCP 428 may implement an "AutoForwardTarget" flag that determines whether the Store-SCP is willing to accept DICOM "pushed" data, also known as a "push". This pushed data may be sent using an unsolicited DICOM C-STORE operation. Such pushed data may come from a user-entered source, an automated source (for example, the date and time of a study may be automatically populated by an enterprise imaging device when the study is collected), a MWL source, or a combination thereof.

Figure 4C:
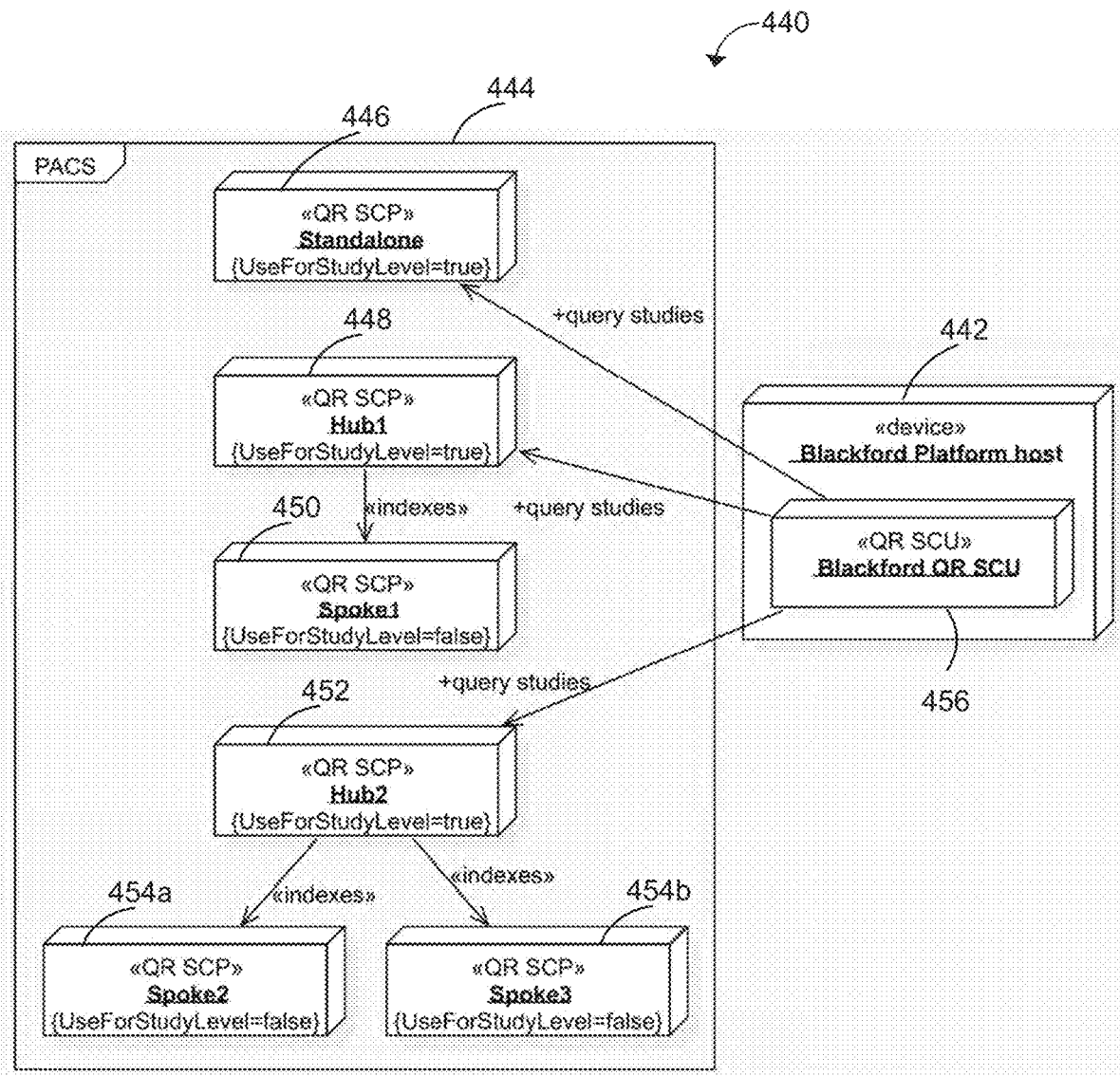
FIG. 4C is a dataflow diagram of a platform that uses polling for discovery of current studies.

In an alternate embodiment (see FIG. 4C), the platform 422 may poll an enterprise imaging system 424, and in response the enterprise imaging system 444 may send new studies, image data, and associated metadata from a QR SCU to a Store SCP of to the platform (see e.g. FIG. 4C)

More generally, the system shown in FIG. 4B may include an enterprise imaging device 424 having two data sources 426*a* and 426*b*. The two data sources 426*a* and 426*b* may be any data source, including but not limited to a PACS server, image acquisition devices such as modalities, MWL, or other enterprise imaging devices.

The enterprise imaging device 424 may be a PACS server, and may have a first Storage Service Class Users (SCU) 426a and a second Storage SCU 426b. The first and the second Store SCUs 426 may send studies to the Store SCP 428 of platform 422 using DICOM push. The enterprise imaging device 424 (such as a PACS server) may push a received study entity generally contemporaneously with its reception at the enterprise imaging device.

The push request of the study entity from the image device 424 may include study metadata. The push request may further include series metadata. The push request may further include image metadata. In one embodiment, the push request may include image data corresponding to the study metadata, the series metadata, and/or the image metadata.

In one embodiment, the push request may be from a PACS server, a MWL system, or directly from an image acquisition device (see e.g. FIG. 1A at 112).

Referring next to FIG. 4C, there is a dataflow diagram 440 of a platform 442 that uses polling for discovery of current studies. The platform 442 may be configurable to define a number of known enterprise imaging devices such as enterprise imaging device 444 that may be polled in order to receive new studies to process. The polling may occur individually for the enterprise imaging devices, and the polling interval may be configurable for each enterprise imaging device. The platform 442 may have an interface 456 capable of sending queries for studies, and receiving image data and associated metadata communicated over a network device for interaction with other enterprise imaging devices. Each of the enterprise imaging devices 444 may have one or more data sources, such as the first data source 446, the second data source 448, the third data source 450, the fourth data source 452, the fifth data source 454a, and the sixth data source 454b; the data sources capable of sending and receiving image data and associated metadata communicated over a network device for interaction with the platform 442. It is understood that the data sources 446, 448, 450, 452, 454a, and 454b and the interface 456 may use any suitable data exchange format.

In this example embodiment, the platform 442 may have a DICOM QR SCU (456) that uses DICOM query-retrieve to poll for metadata from the enterprise imaging device 444.

In this DICOM example, the enterprise imaging device may be a PACS server 444 and may have a first data source that is a standalone QR SCP 446, a second data source that is a first hub QR SCP 448, a third data source that is a first spoke QR SCP 450 providing an index for the first hub QR SCP 448, a fourth data source that is a second hub QR SCP 452, a fifth data source that is a second spoke QR SCP 454a providing an index for the second hub QR SCP 452, and a sixth data source that is a third spoke QR SCP 454b providing an index for the second hub QR SCP 452. The SCPs of the PACS server 444 may be Query/Retrieve SCPs. As indicated, a hub may index a spoke by maintaining an index of the data stored at the spoke. This indexing may provide for fast service of queries of the indexed data. The hub may index the metadata of the spoke, or both the metadata and the image data of the spoke. The platform may query a hub to determine what metadata and associated image data is available, including the location where the metadata and associated image data are stored within the. Once the location is queried, the platform may then direct retrieve requests to one or more spoke servers identified in the hub's query response.

The platform 442 may send a poll request to enterprise imaging device 444 to request new studies. The poll request may be from the platform 442 to the data sources including the standalone QR SCP 446, the first hub QR SCP 448, or the second hub QR SCP 452 (or a combination thereof). In the case of a DICOM environment, the polling requests may be sent from the platform 442 using DICOM C-FIND commands to the SCPs. The platform 442 may be configured to identify data sources at enterprise imaging devices to be polled using the a local flag "UseForStudyLevel=true", which may indicate that the data source at the enterprise imaging device is a valid polling target.

In response to the poll request from the platform, one or more of the data sources (the SCPs) may respond with study metadata, series metadata, or image metadata (or a combination thereof).

Figure 4D:
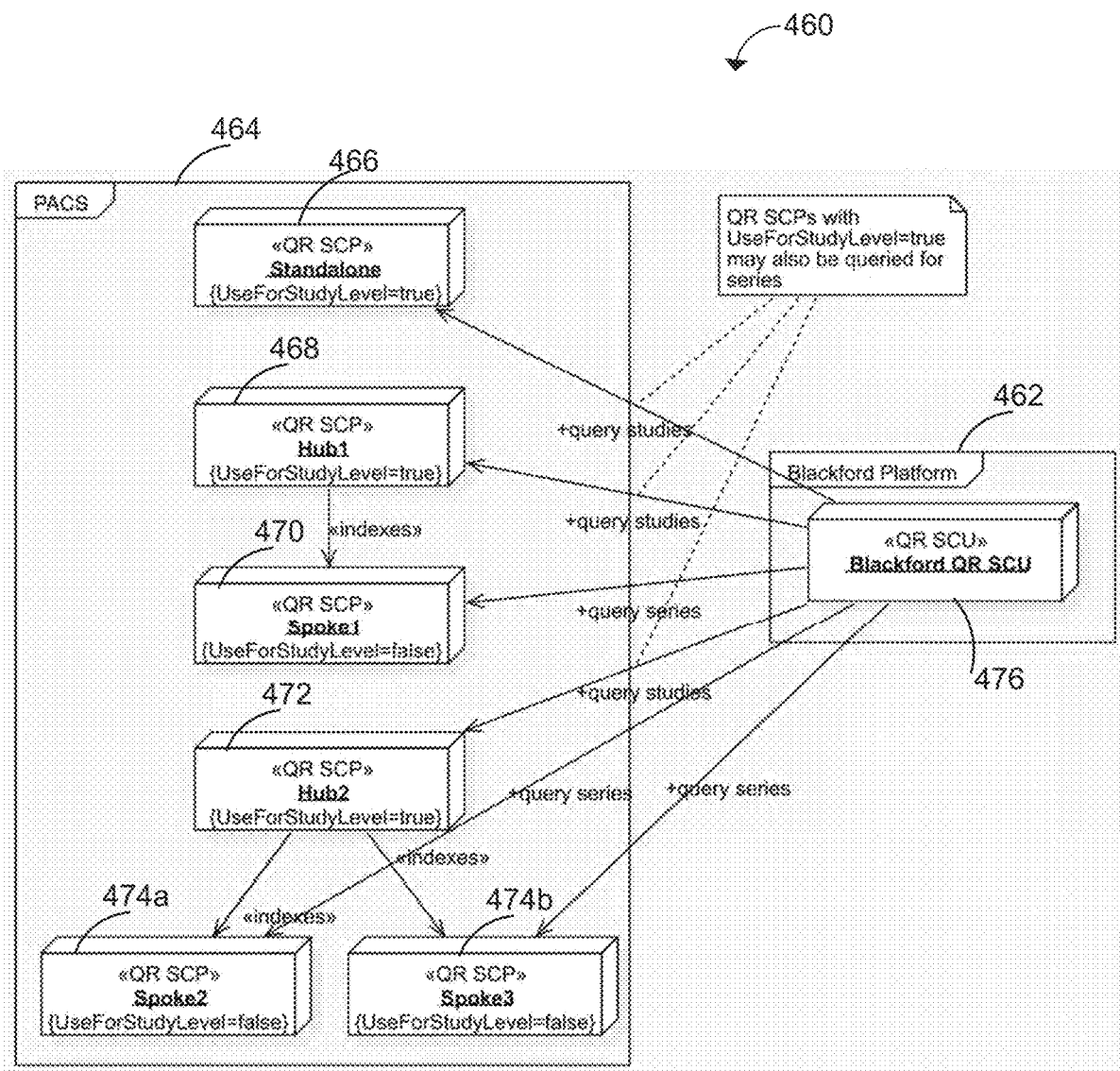
FIG. 4D is a dataflow diagram of a platform for discovery of prior studies.

Referring next to FIG. 4D, there is shown a dataflow diagram of a system for discovery of prior studies. The platform 462 may have an interface 476 capable of sending and receiving image data and associated metadata communicated over a network device for interaction with other enterprise imaging devices. The enterprise imaging device 464 may have one or more data sources such as a first data source 466, a second data source 468, a third data source 470, a fourth data source 472, a fifth data source 474a, and a sixth data source 474b, the data sources capable of sending and receiving image data and associated metadata communicated over a network device for interaction with the platform 462. The platform 462 may send a query message to one or more of the data sources to locate studies, and may further send a query message to one or more of the data sources to located series. It is understood that the data sources 466, 468, 470, 472, 474a, and 474b and the interface 476 may use any suitable data exchange format.

In an example embodiment where the platform 462 and the enterprise imaging device 464 use DICOM, the platform may have an interface that is a QR SCU 476. The enterprise imaging device may be a PACS server 464, having a data source that is a standalone SCP 466, a second data source that is a first hub QR SCP 468, a third data source that is a first spoke QR SCP 470 that provides an index for the first hub QR SCP 468, a fourth data source that is a second hub QR SCP 472, a fifth data source that is a second spoke QR SCP 474a that provides an index for the second hub QR SCP 472, and a sixth data source that is a third spoke QR SCP 474b that provides an index for the second hub QR SCP 472.

The platform 462 may apply a set of rules for one or more clinical software applications to the current study metadata that is received, and based on the rules may subsequently send a prior study query for candidate prior studies to the standalone SCP 466, the first hub QR SCP 468 and the second hub QR SCP 472. Each of the standalone QR SCP 466, first hub QR SCP 468, and the second hub QR SCP 472 may send a prior study response based on the prior study query to the platform 462. The prior study response may include one or more candidate prior studies. The one or more candidate prior studies each having study metadata, series metadata, or image metadata, or a combination thereof. The platform 462 may then apply rules to the one or more candidate prior studies based on the received study metadata, series metadata, image metadata, or the combination thereof. The platform may then send a series query to the first spoke QR SCP 470, the second spoke QR SCP 474a, and the third spoke QR SCP 474b. The first spoke QR SCP 470, the second spoke QR SCP 474a and the third spoke QR SCP 474b may then send a series response to the platform 464 comprising series metadata, image metadata, or a combination thereof.

Figure 4E:
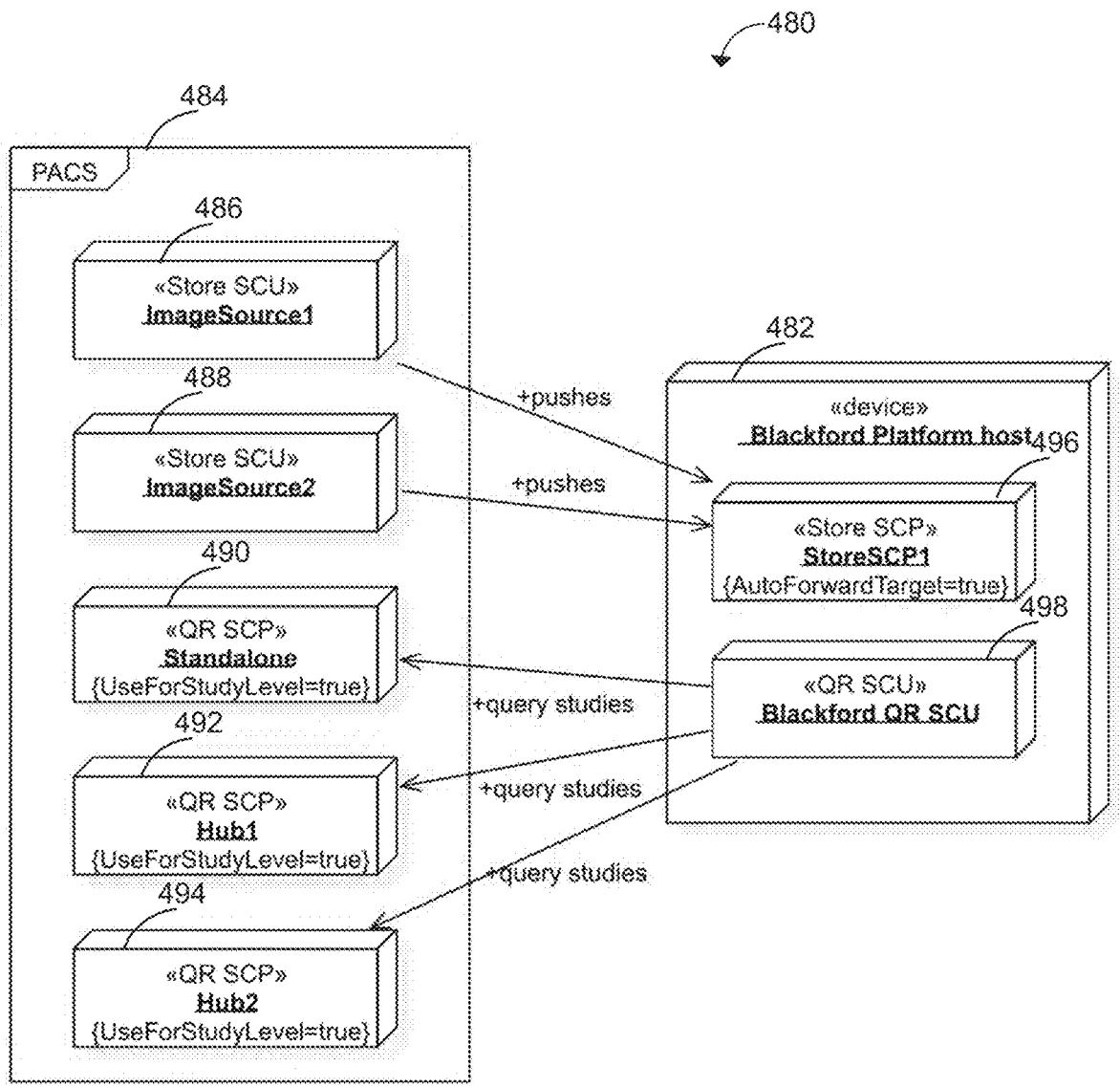
FIG. 4E is a dataflow diagram of a platform that uses both auto-forwarding and polling for discovery of current studies.

Referring next to FIG. 4E, an alternate embodiment showing a dataflow diagram 480 of a platform 482 that uses both pushing and polling for discovery of new studies. Platform 482 may have a first interface 496 and a second interface 498 capable of sending and receiving image data and associated metadata communicated over a network device for interaction with other enterprise imaging devices. The enterprise imaging device 484 may have one or more data sources such as first data source 486, second data source 488, a third data source 490, fourth data source 492, and a fifth data source 494, the data sources capable of sending and receiving image data and associated metadata communicated over a network device for interaction with the platform 482. The data sources 490, 492, 494 may be configured at the platform 482 with a "UseForStudyLevel=true" flag, and this flag may indicate to the platform 482 whether a particular data source has capabilities for answering study level queries. It is understood that the data sources 486, 488, 490, 492, and 494 and the interfaces 496 and 498 may use any suitable data exchange format.

In an example embodiment where the platform 482 and the enterprise imaging device 484 use DICOM, the first interface may be a Store SCP 496 and the second interface may be a Query/Retrieve SCU 498. The enterprise imaging device 484 may have a first data source that is a Store SCU 486, a second data source that is a Store SCU 488, a third data source that is a standalone QR SCP 490, a fourth data source that is a first hub QR SCP 492, and a fifth data source that is a second hub QR SCP 494.

In this embodiment, the functionality of both FIGS. 4B and 4C is combined. This is accomplished by configuring platform 482 to include data sources including standalone QR SCP 490, first hub QR SCP 492, and second hub QR SCP 494, and the platform 482 sends polling requests to them to locate new studies as described in FIG. 4B4C.

The first data source SCU 486 and the second data source SCU 488 are configured to auto-forward incoming studies to the platform 482 as described in FIG. 4C4B.

Figures 5A, 5B:
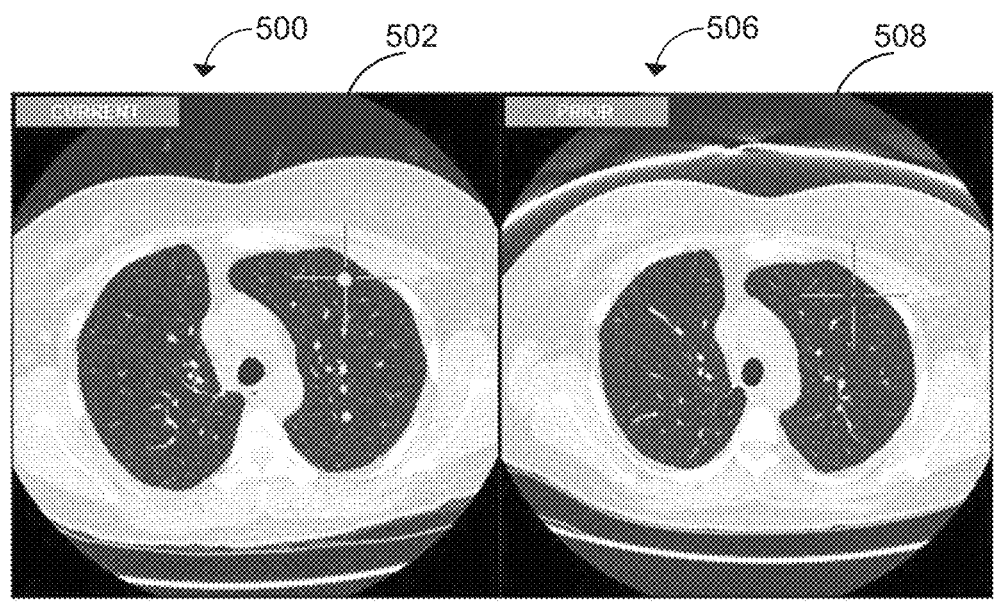
FIG. 5A is an example of medical image data of a current study.
FIG. 5B is an example of medical image data of a prior study corresponding to the current study.

Referring to FIG. 5A, there is shown a diagram 500 of an example of medical image data 502 of a current study. The medical image data 502 of the current study may be an image collected by a MRI image acquisition device. The image data may be collected in a variety of image formats as described herein.

Referring to FIG. 5B, there is shown a diagram 506 of an example of medical image data 508 of a prior study corresponding to the current study in FIG. 5A. The medical image data 508 of the current study may be an image collected by a MRI image acquisition device. The image data may be collected in a variety of image formats as described herein.

Figure 5C:
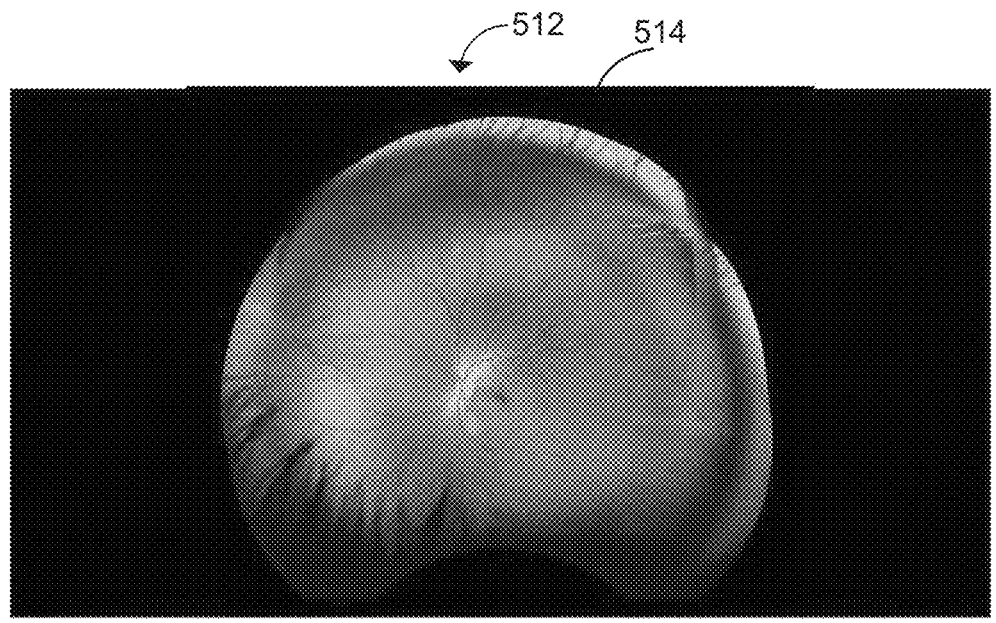
FIG. 5C is another example of medical image data.

FIG. 5C is another example of medical image data. FIG. 5C shows a composite image 512 of a patient's eye. The, constructed from five overlapping images of a patient's eye 514. The composite image 512 may be collected using an acquisition technique such as "3D optical coherence tomography", or "3D OCT"; where images are taken with the patient looking up, down, left, right and straight ahead, and then combined to form a "montage".

Figure 5D:
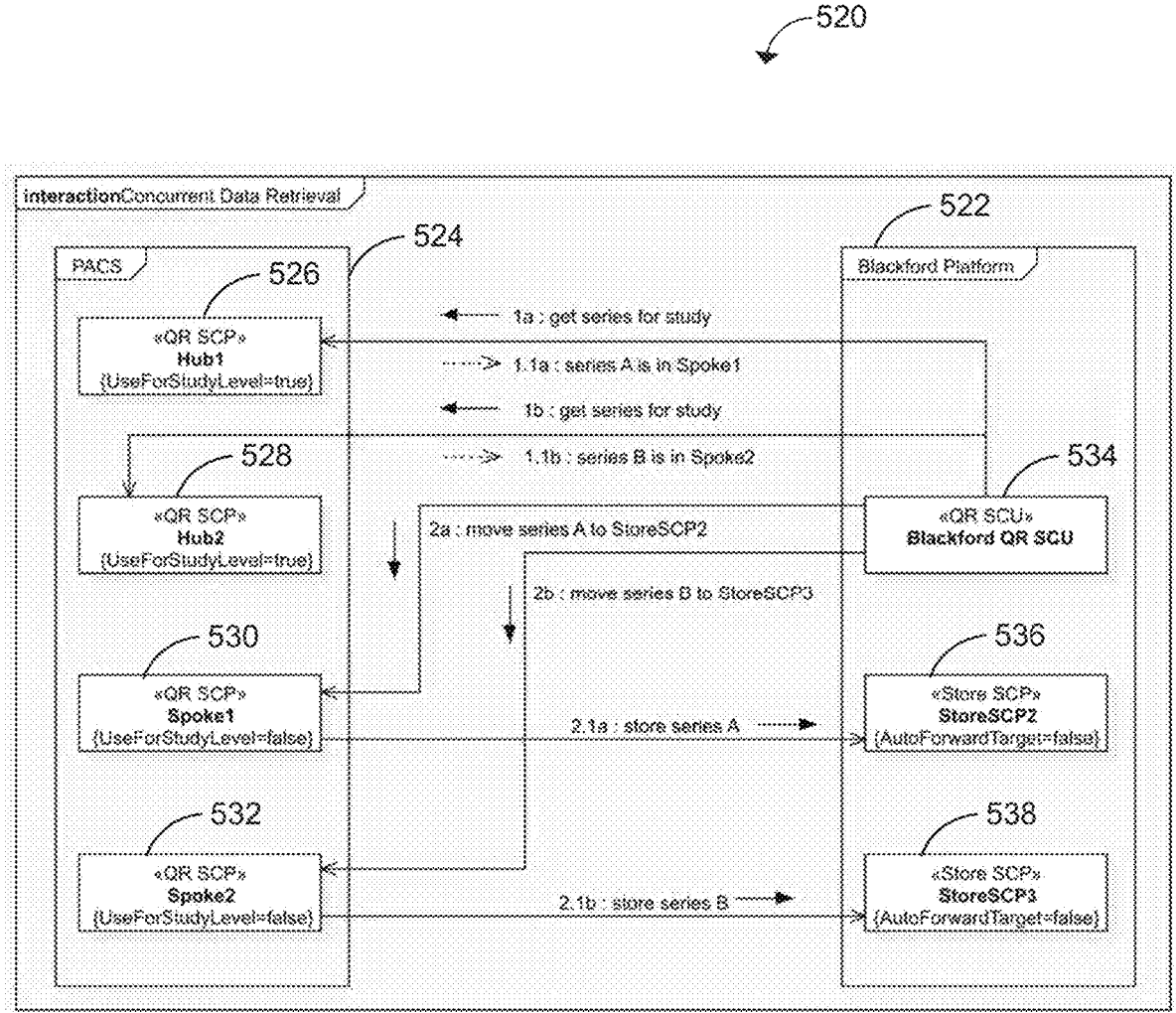
FIG. 5D is a dataflow diagram of a platform transferring medical image data.

FIG. 5D is a dataflow diagram 520 of the platform 522 when transferring medical image data. The platform 522 may determine if a current study, prior studies, series, images (or a combination thereof) match a clinical software application based on the metadata associated with the current study, prior studies, series, images, or the combination thereof. The matching current study, prior studies, series, images, or the combination thereof may have associated image data that may be collected and combined by the platform 522 into a matched study set.

The platform 522 may have one or more interfaces, such as a first interface 534, a second interface 536, and a third interface 538 capable of sending and receiving image data and associated metadata communicated over a network device for interaction with other enterprise imaging devices.

The enterprise imaging device 524 may have one or more data sources, such as a first data source 526, a second data source 528, a third data source 530, and a fourth data source 532, the data sources capable of sending and receiving image data and associated metadata communicated over a network device for interaction with the platform 522. It is understood that the data sources 526, 528, 530, and 532 and the interfaces 536 and 538 may use any suitable data exchange format.

In an example embodiment where the platform 522 and the enterprise imaging device 524 use DICOM, the first interface may be a QR SCU 534, the second interface may be a first Store SCP 536, and the third interface may be a second store SCP 538. The enterprise imaging device 524 may be a PACS server, having a first data source that is a first hub QR SCP 526, a second data source that is a second hub QR SCP 528, a third data source that is a first spoke QR SCP 530, and a fourth data source that is a second spoke QR SCP 532. The first hub QR SCP 526 and the second hub QR SCP 528 may be configured for polling at the platform 522 by using a UseForStudyLevel=true flag as described above.

In order to receive the image data associated with the matching current study, prior studies, series, images, or the combination thereof, the platform 522 may request series data for a current or prior study from the first hub QR SCP 526 (see 1a) and the second hub QR SCP 528 (see 1b). This may be in the form of a C-FIND DICOM message. The first hub QR SCP 526 may respond to the request by sending series A metadata to the platform 522 (see 1.1a). The second hub QR SCP 528 may respond to the request by sending series B metadata to the platform 522 (see 1.1b). The first hub QR SCP 526 and the second hub QR SCP 528 may identify the image data source as another data source such as the first spoke QR SCP 530 or the second spoke QR SCP 532.

The platform 522 may then request image data corresponding to the series A metadata and the series B metadata. This may be done using a C-MOVE DICOM command, and may be sent to the data source identified by the C-FIND DICOM command. The C-MOVE DICOM command (see 2a) may request that the first spoke QR SCP 530 performs a copy of image data to the platform 522, and the first spoke QR SCP 530 may copy the requested image data to the platform 522 in response to the C-MOVE DICOM command (see 2.1a). Another C-MOVE DICOM command (see 2b) may request that the second spoke QR SCP 532 perform a copy to the platform 522, and the first spoke QR SCP 530 may copy the requested image data to the platform 522 in response to the C-MOVE DICOM command (see 2.1b).

In one embodiment of FIG. 5D, the concurrent retrieval of image data may be performed. Specifically, two Store SCPs may be used to receive two different series at the same time.

Figure 5E:
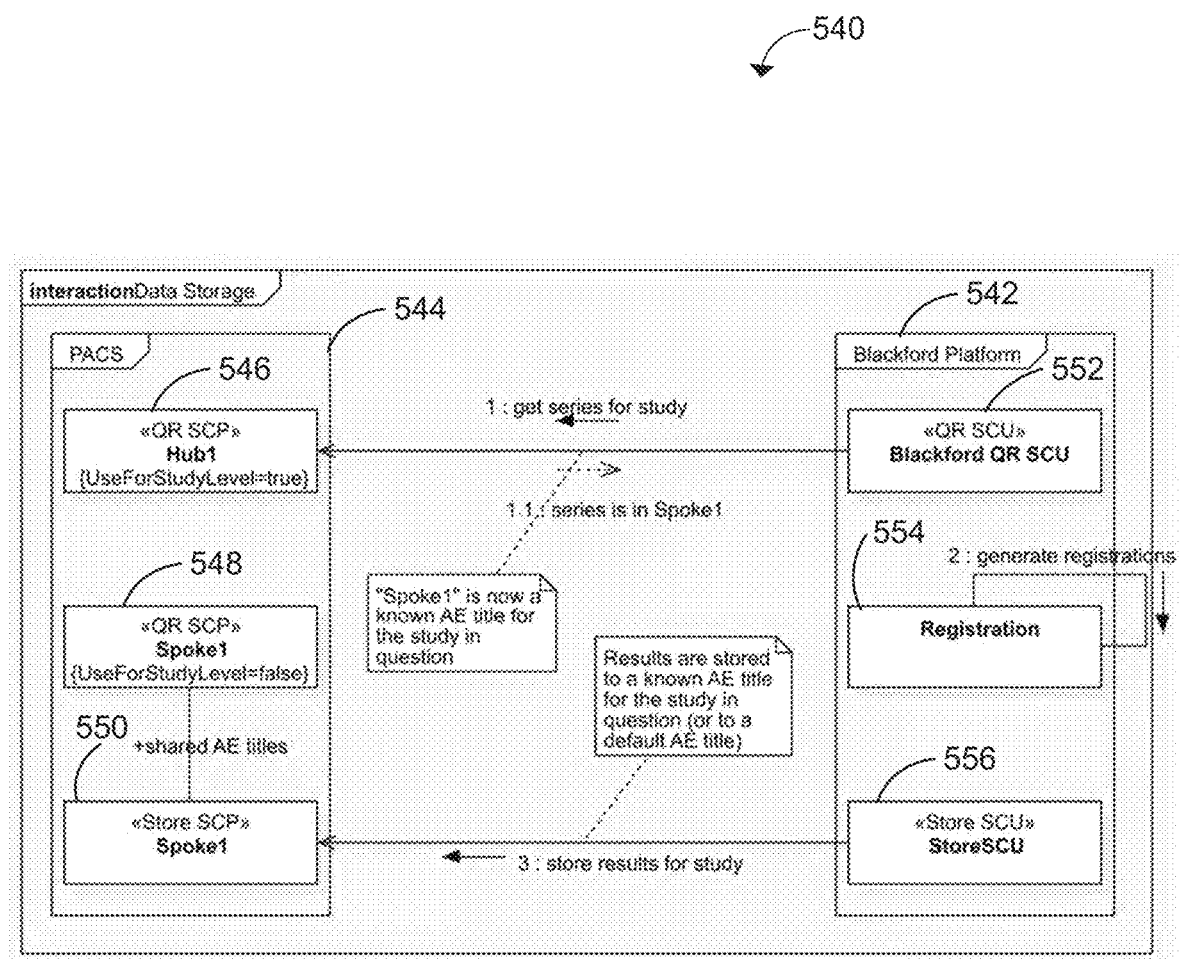
FIG. 5E is a dataflow diagram of a platform storing medical image data and associated metadata.

Referring next to FIG. 5E, shown therein is a dataflow diagram of a platform 542 storing medical image data and associated metadata. The platform 542 may have a first interface 552, a clinical software application 554, and a second interface 556 capable of sending and receiving image data and associated metadata communicated over a network device for interaction with other enterprise imaging devices. The enterprise imaging device 544 may have a first data source 546, a second data source 548, and a third data source 550, the data sources capable of sending and receiving image data and associated metadata communicated over a network device for interaction with the platform 542. The enterprise imaging device 544 may have a first data sink 550, capable of receiving image data and associated metadata for storage communicated over a network device for interaction with the platform 542. It is understood that the data sources 546, 548, and 550, the interfaces 552 and 556, and the clinical software application 554 may use any suitable data exchange format.

In the example embodiment where the platform 542 and the enterprise imaging system 544 communicate using the DICOM standard, the platform 542 may have a first interface that is a QR SCU 552, a clinical software application that is a registration application 554, and a second interface that is a store SCU 556. The enterprise imaging device may be a PACS server 544 that has a first data source that is a first hub QR SCP 546, a second data source that is a first spoke QR SCP 548, and a third data source that is a first spoke Store SCP 550. The first spoke QR SCP 548 and the first spoke Store SCP 550 may be two interfaces for the same component, where the QR SCP 548 may be for query retrieve functionality and the Store SCP 550 may be for storing studies.

Once the platform 542 has submitted the assembled matched study set and the image data corresponding to the assembled matched study to a clinical software application 554, the clinical software application 554 begins processing. In this example, the clinical software application 554 as shown is a registration clinical software application. Once complete, the clinical software application 554 will send a processed study back to the platform 542 so the platform can route the processed study accordingly. For example, the first hub QR SCP 546 may receive a request for a series from the platform 542, and the first spoke may send the series metadata and image data associated with the series metadata to the Query/Retrieve SCU 552 of platform 542. The assembled matched study set including the series metadata and the image data may be processed by clinical software application 554, and the processed study may be sent back to platform 542. The Store SCU 556 of platform 542 may then send the processed study to the first spoke QR SCP 550 of the enterprise imaging device 544, where the processed study may be stored. The processed study may include one or more processed series, and one or more processed images, including metadata and image data associated with the one or more processed series and the one or more processed images.

Figure 6A:
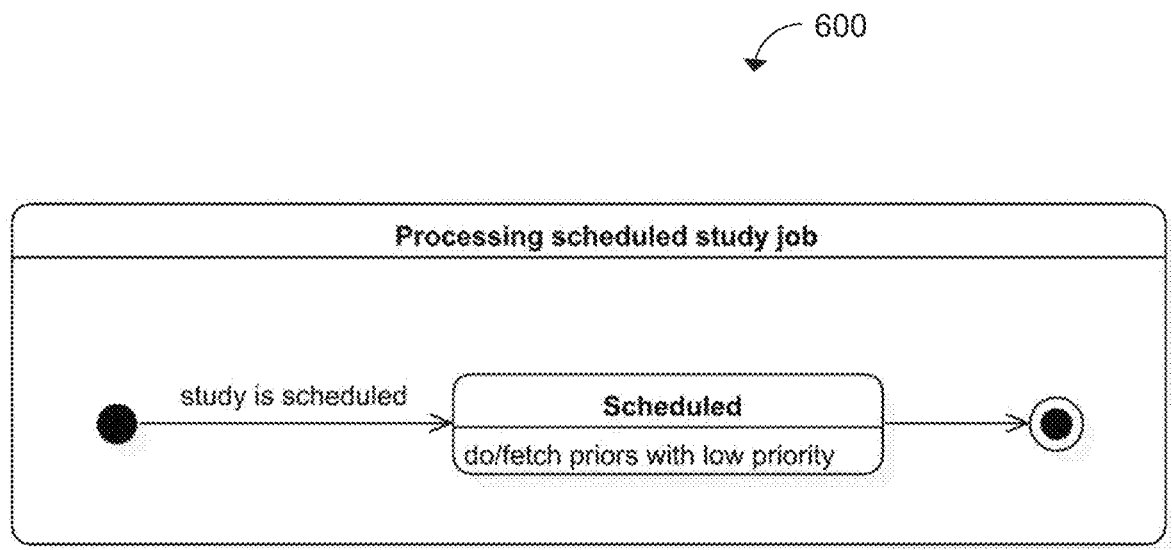
FIG. 6A is a processing diagram for a study.
Figure 6B:
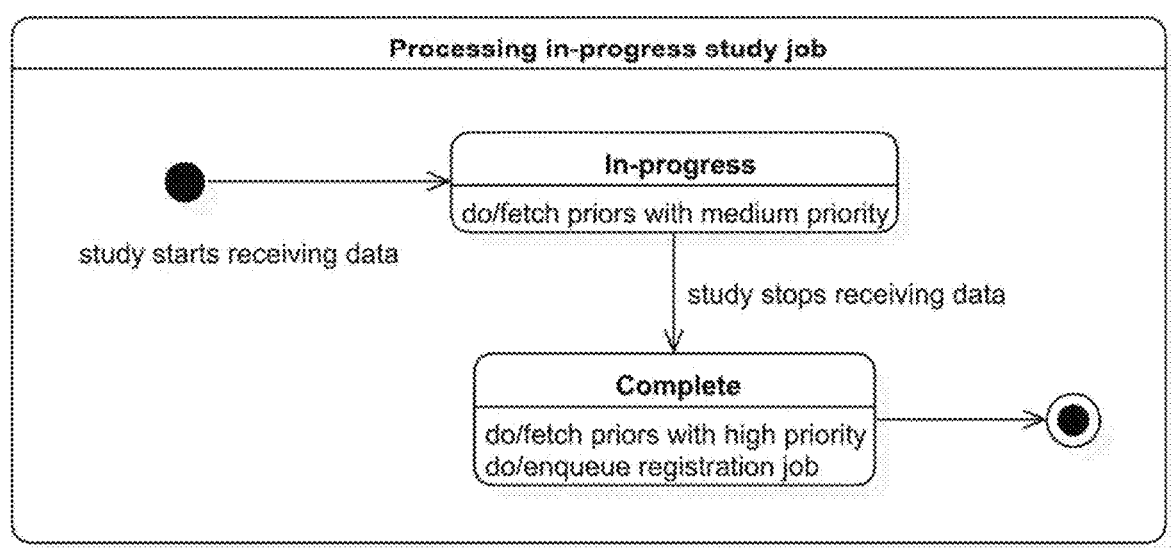
FIG. 6B is a processing diagram for an in-progress study.

Referring next to FIGS. 6A and 6B, there is shown a processing diagram 600 for a study, and another processing diagram 620 for an in-progress study. Studies received at the platform may be referred to as current studies. The current studies are sent by an enterprise imaging device, for example a PACS server or an MWL server. The platform may process incoming current studies by way of "jobs". The jobs may be scheduled or driven by discrete events in the lifecycle of the associated study. For example, if a current study is scheduled via MWL, a new job may be created and started. As part of this job, the platform may discover prior studies (by querying one or more medical devices), determine the relevance of received prior studies using relevancy rules, and fetch related images corresponding to the prior metadata. The current study and its prior studies are scheduled for processing at the clinical software application.

In another embodiment, when a current study is being collected at an image acquisition device and the enterprise imaging device (or PACS server) and the platform start receiving image data, a new job is started. As part of this job, the Platform may discover new data, determine the relevance of the new data, including new images and prior studies, and fetch any missing prior data. When the current study finishes receiving image data, the Platform fetches any missing current and/or prior data at high priority.

Once all data has been fetched, the current study and its prior studies are scheduled for processing at the clinical software application.

Figure 6C:
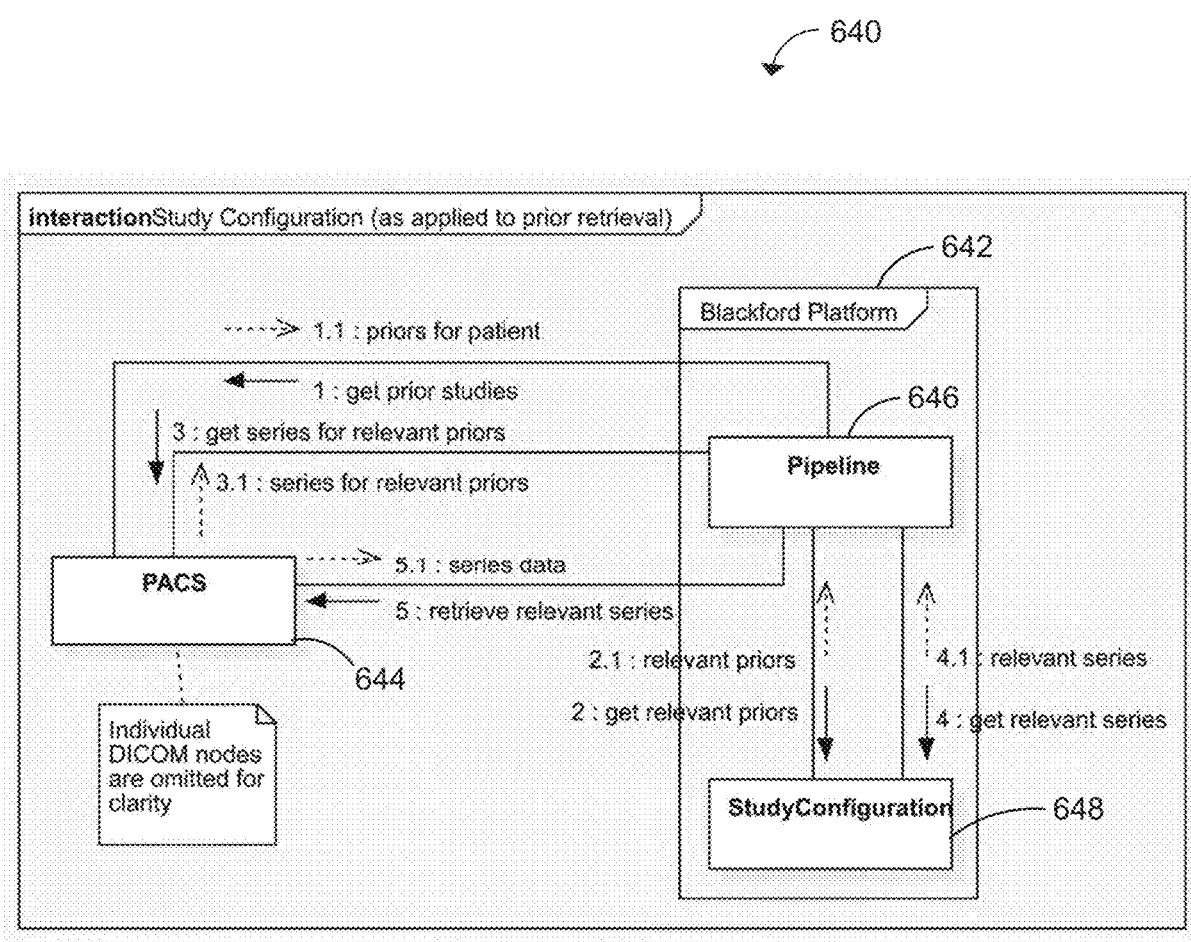
FIG. 6C is a dataflow diagram of a platform applying a matching rule for a clinical software application.

Referring next to FIG. 6C, there is shown a dataflow diagram 640 of the platform 642 applying a matching rule for a clinical software application. The platform 642 may have pipeline 646 and study configuration 648. A enterprise imaging device 644 such as a PACS server or a medical imaging archive and may be in network communication with the platform 642. The platform 642 may receive a current study in pipeline 646. The platform 642 may determine if the current study is relevant to one or more clinical software applications based on one or more relevancy rules in their configurations. The pipeline 646 of platform 642 may request metadata for prior studies of the current matched study from the enterprise imaging device 644 such as a PACS server. The enterprise imaging device 644 may send metadata for one or more candidate prior studies to the platform 642. Relevant prior studies may be determined by applying one or more prior relevancy matching rules associated with the rule matching the current study in the clinical software application configuration. This may be accomplished by first requesting the one or more prior relevancy rules from the study configuration 648 and applying the one or more prior relevancy rules to the one or more candidate prior studies. Relevant series associated with the relevant priors may be determined by requesting the series metadata from the enterprise imaging device 644 for the matching prior studies. The enterprise imaging device 644 may send metadata for candidate prior series to the platform 642, which may apply one or more prior series matching rules to determine one or more matched prior series. The image data associated with the one or more matched prior series may then be requested from the enterprise imaging device 644 by the platform 642 and an assembled matched study set may be generated for processing by a clinical software application.

In this manner, relevant image data to the current study is retrieved and non-relevant or irrelevant data is not retrieved.

Figure 7A:
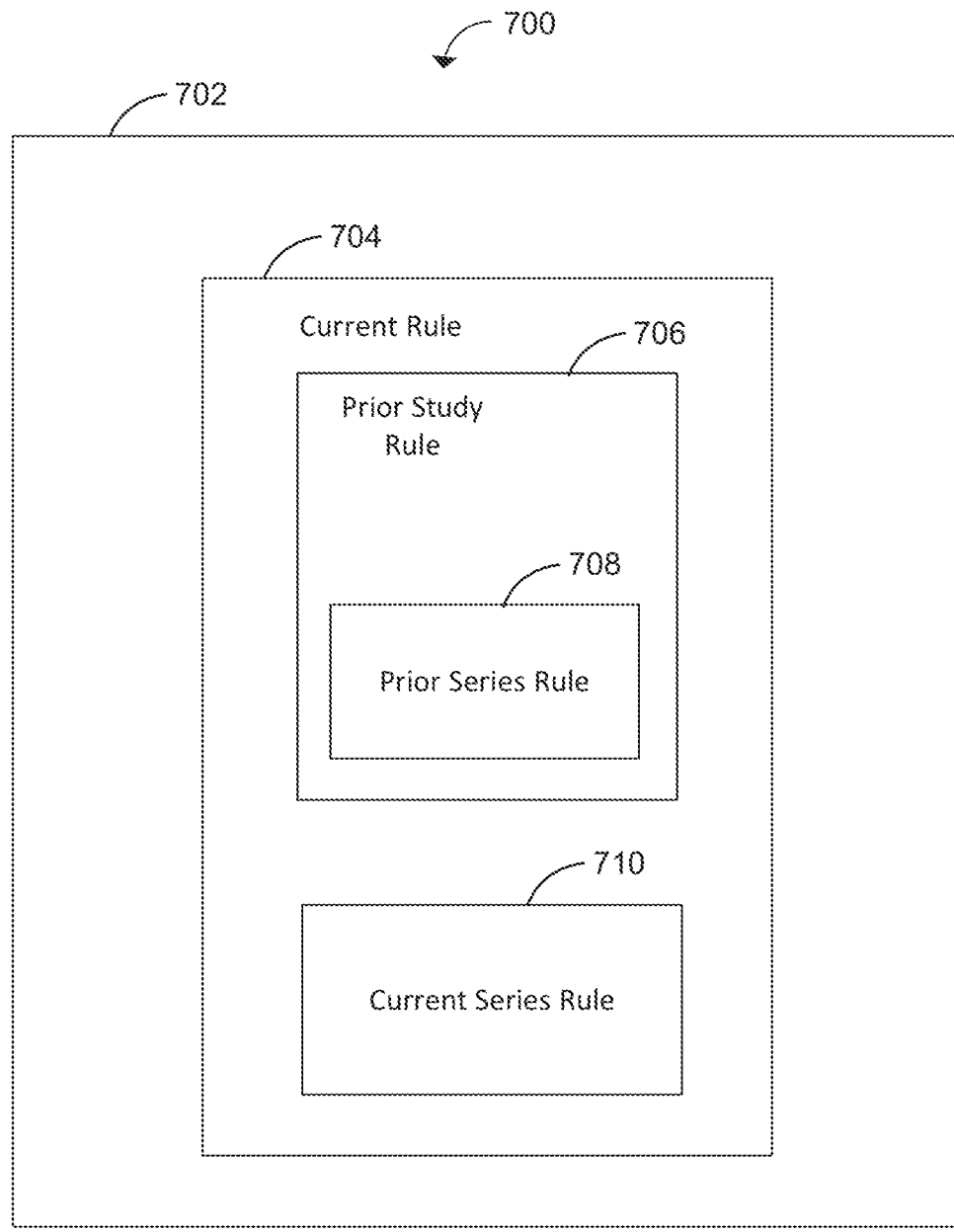
FIG. 7A is a software component diagram of a matching rule for a clinical software application.

Referring next to FIG. 7A, shown therein is a software component diagram of a matching rule for a clinical software application. A clinical software application may have a set of relevancy rules 702 associated with its configuration. The platform may maintain a set of rules that may be shared between the one or more clinical software applications that are configured at the platform to process incoming medical data.

The set of relevancy rules 702 for the clinical software application define a set of current study matching rules that define whether a current study is a matching current study. Each current rule 704 may have one or more prior study matching rules 706 that may function to determine whether any prior studies associated with the current study match the current study and should be used when processing the assembled matched study set at the particular clinical software application. Furthermore, each of the prior study matching rules 706 may have one or more prior series matching rules 708. These rules may be used once a candidate prior study is located to determine whether the candidate prior study is a matching prior study. Furthermore, each of the current study matching rules 704 may have one or more current series matching rules 710, such that when a current study is received by the platform, the current series matching rules 710 may be applied to any current series associated with the current study to determine if it's a matching current study.

Each of the current study rules, prior study rules, prior series rules, and current series rules may use pattern matching against any metadata associated with the current study, prior studies, prior series or current series.

Referring to FIG. 7B, there is shown a diagram 750 of an example matching rule of a of a study configuration of a clinical software application. The study configuration 752 may be used to configure a clinical software application to identify which studies and series are suitable for processing by the clinical software application, whether as current or prior. The study configuration 752 may provide for configuration for rejecting irrelevant patients (for example, those lacking a name or a valid patient ID), marking current studies as relevant for processing, selecting relevant prior studies associated with a current marked as suitable for processing, labelling studies with metadata tags for the purposes of processing, selecting appropriate series for processing within relevant studies, and dispatching them for processing.

The study configuration is shown in XML, but may be prepared in any other data configuration format as is known. The study configuration may also be created using a GUI, such as via a web application form.

As shown in FIG. 7B, it is understood that placeholder elements including curly braces are visible to identify placeholder expressions.

The study attributes of the study configuration are as follows.

If it is present, maximum RelevantStudyCount defines the maximum number of studies that will be processed when a current study becomes unchanged for a period of time. For example, if a single current study has 5 relevant priors but maximumRelevantStudyCount is set to 3, only the current study and the 2 most recent priors will be processed.

If it is present and set to false, processSingleStudies indicates that in the case where only a single study is considered to be relevant (that is, a current study has no relevant priors), that study should not be processed.

If it is present, timeBasedStudyRelevancyCutoff defines a time span. If the platform has not started a job for a current study for a particular clinical software application within this time span of having received the current study, the job will be dropped, and no processing will occur. This may be to allow the platform to 'catch up', in the case of high job latency by dropping jobs which are no longer useful to produce registrations in favour of newer jobs. If it is present, calledAeTitles defines a regular expression to which a study calledAeTitle attribute may be matched in order to be considered relevant.

Within the study configuration 752, there may be further relevancy rules defined. Within the parent <studyConfiguration/> element, a single <relevancyMap/> element may be used to select currents and priors for processing.

In the relevancyMap, there may be zero or more <study/> rules specified within the top-level <relevancyMap> element.

The study rule attributes may provide the following functions. The mandatory name attribute may provide a descriptive name for logging purposes and it must uniquely identify each rule. If it is present, the description may define a regular expression used to select studies based on the DICOM Study Description tags. Matches may be performed case insensitively.

If present, containedModalities may define a comma-separated set of DICOM modality strings. This may determine a match if any defined modality matches those present in the study's DICOM Modalities in Study attribute.

If present, minimumInstanceCount may define the minimum number of images desired before a study is considered relevant.

The mandatory priors attribute may identify named <study/> rules that are considered to be relevant priors for the current <study/> rule. Values may include*(in which case any matching <study/> rule is a relevant prior), or a comma-separated list of <study/> rule names. The current rule may itself be identified as a valid prior, along with any other rules that define overlapping anatomical regions.

If it is present, priority may define an integer priority value for the <study/> rule.

Within each <study/> rule, there may be zero or more <series/> rules that may be specified.

The study rules may have attributes as follows.

The mandatory name attribute may provide a descriptive name for logging purposes.

If it is present, bodyPartExamined may define a regular expression that is matched against the series' DICOM Body Part Examined values.

If it is present, the description defines a regular expression that may be used to select studies based on the DICOM Series Description tags. Matches may be performed case insensitively.

If it is present, minimumInstanceCount may define the minimum number of images required before a series is considered relevant.

If it is present, modality may define a DICOM modality value that may be compared to the series' DICOM Modality value.

If it is present, seriesNumber may define a value that is compared to the series' DICOM Series Number value.

If it is present, action may define a single series-level "action" keyword. This may be used to inform the platform of how to process incoming series.

Referring next to FIG. 7C, there is shown a diagram 760 of an example configuration of a study matching rule where that matches CT studies of the lower extremities (i.e. legs).

Referring next to FIG. 7D, there is shown a diagram 780 of another an example configuration of a set of study matching rules.

Figure 8A:
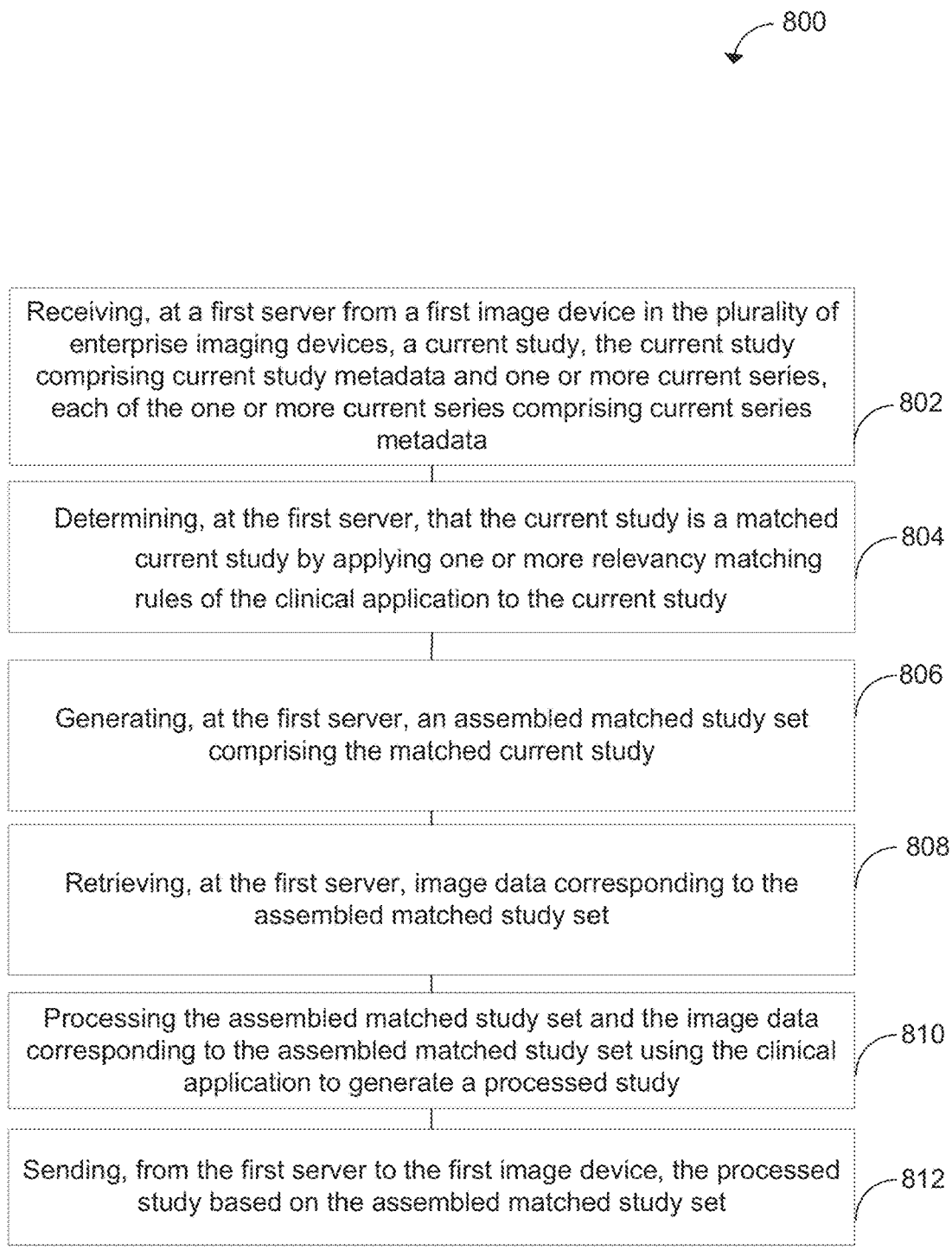
FIG. 8A is a method diagram for processing medical data.

Referring next to FIG. 8A, there is shown a method diagram 800 for processing medical data. The method 800 is for processing a plurality of medical images from a plurality of enterprise imaging devices using a clinical software application. The metadata associated with the current study, the matched prior study, and the prior series of the one or more matched prior series may be in either a DICOM format and a HL7 format.

At 802, receiving a current study at a first server from a first image device in the plurality of enterprise imaging devices, the current study comprising current study metadata and one or more current series, each of the one or more current series comprising current series metadata. The current study may be received from at least one of a Picture Archiving and Communication System (PACS server) server and a Modality Worklist server.

In one embodiment, the current study may be pushed (or auto-forwarded) to the first server from a PACS server or a MWL server, or alternatively from an image acquisition device.

In another embodiment, the first server may send a polling request to the PACS server, the polling request for a new current study. Further, the first server may send a second polling request for a new current study to an MWL.

At 804, determining, at the first server, that the current study is a matched current study by applying one or more relevancy matching rules of the clinical software application to the current study. In one embodiment, the determination that the current study is a matched current study may further include sending, from the first server to each of the plurality of enterprise imaging devices, a query for one or more candidate prior studies based on the matched current study, the one or more candidate prior studies each comprising prior study metadata and one or more prior series, each of the one or more prior series comprising prior series metadata; receiving, at the first server from at least one enterprise imaging devices of the plurality of enterprise imaging devices, the one or more candidate prior studies; determining, at the first server, that the one or more candidate prior studies are one or more matched prior studies by applying the one or more relevancy matching rules of the clinical software application to the one or more candidate prior studies; wherein the assembled matched study set further comprises the one or more matched prior studies.

At 806, generating, at the first server, an assembled matched study set comprising the matched current study.

At 808, retrieving, at the first server, image data corresponding to the assembled matched study set.

At 810, processing the assembled matched study set and the image data corresponding to the assembled matched study set using the clinical software application to generate a processed study.

At 812, sending, from the first server to the first image device, the processed study based on the assembled matched study set.

In an alternate embodiment, the relevancy matching rules may match based on image metadata. In this embodiment, the matched current study may further comprise one or more matched image metadata portions, each of the one or more matched image metadata portions may correspond to an image in the current study; and the one or more relevancy matching rules may perform pattern matching based on the current study metadata and the one or more matched image metadata portions; the matched prior studies may further comprise one or more matched prior image metadata portions, each of the one or more matched prior image metadata portions corresponding to an image in the matched prior studies; and the one or more relevancy matching rules may perform pattern matching based on the one or more candidate prior studies metadata and the one or more matched prior image metadata portions.

In another embodiment, the current study may be received at the platform along with image data, instead of retrieving the image data subsequently from the metadata. In this embodiment the current study may further comprise current study image data; the one or more candidate prior studies may further comprise candidate prior studies image data; and the one or more candidate prior series may further comprise candidate prior series image data.

Figure 8B:
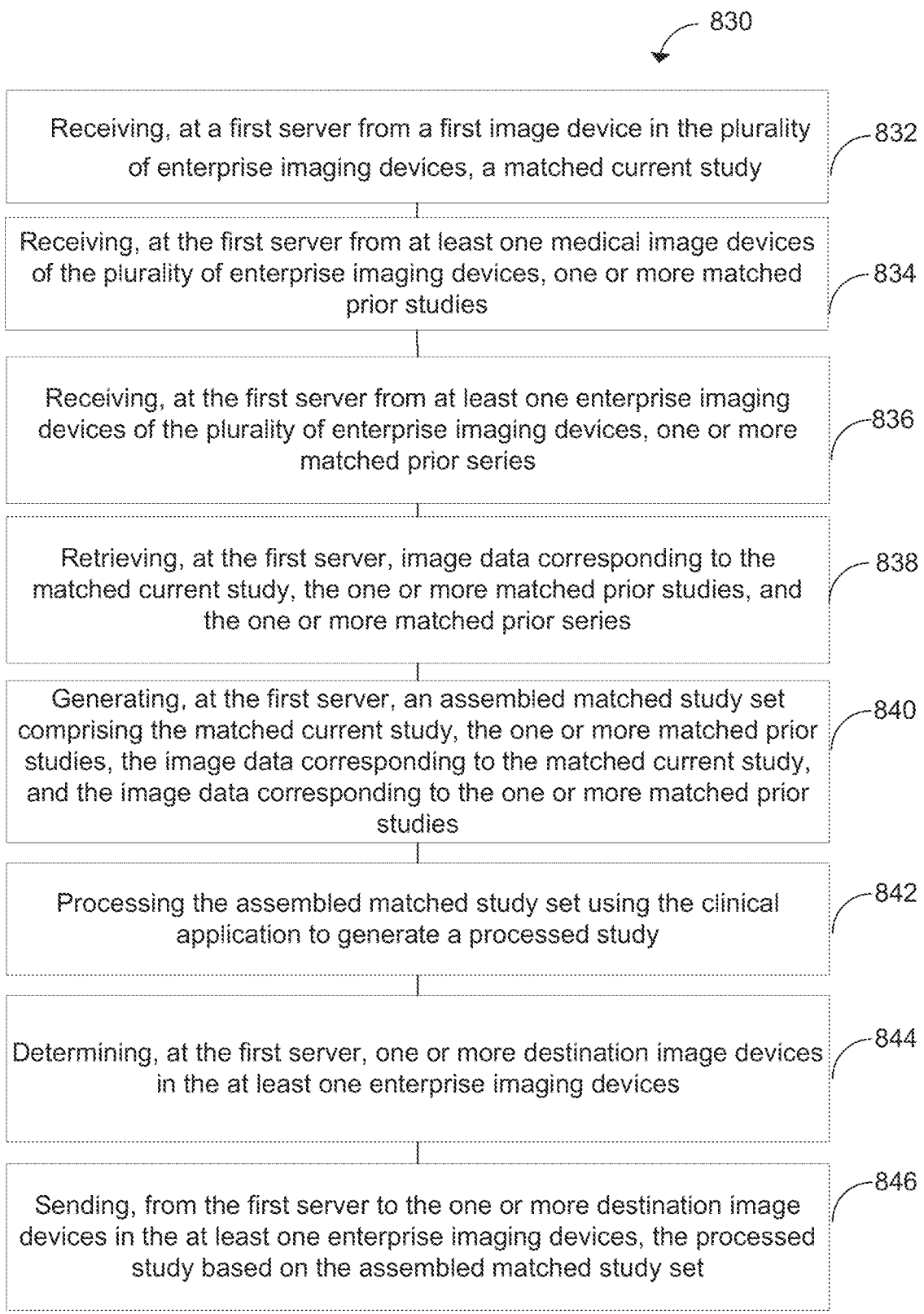
FIG. 8B is another method diagram for processing medical data.

Referring next to FIG. 8B, there is shown a method diagram 830 for processing medical data. The method 830 is for processing a plurality of medical images from a plurality of enterprise imaging devices using a clinical software application. The method 830 may describe where the platform may further determine, based on the assembled matched study set, where to send the subsequently generated processed study.

At 832, a matched current study is received at a first server from a first image device in the plurality of enterprise imaging devices.

At 834, one or more matched prior studies are received at the first server from at least one enterprise imaging devices of the plurality of enterprise imaging devices.

At 836, one or more matched prior series are received at the first server from at least one enterprise imaging devices of the plurality of enterprise imaging devices.

At 838, retrieving, at the first server, image data corresponding to the matched current study, the one or more matched prior studies, and the one or more matched prior series.

At 840, generating, at the first server, an assembled matched study set comprising the matched current study, the one or more matched prior studies, the image data corresponding to the matched current study, and the image data corresponding to the one or more matched prior studies.

At 842, processing the assembled matched study set using the clinical software application to generate a processed study.

The processed study may include one or more processed series, one or more processed images, including metadata and image data associated with the one or more processed series and the one or more processed images.

The processed study may include modality worklist data and modality worklist metadata. The processed study may further include result data, and the first server may store the result data in a database.

The processed study may be in the same metadata format as the assembled matched study set that is used as input for the clinical software application, or it may be in another format.

At 844, determining, at the first server, one or more destination image devices in the at least one enterprise imaging devices.

In one embodiment, the determining the one or more destination image devices in the at least one enterprise imaging devices may further comprise associating the processed study with the matched current study; identifying the one or more destination image devices based on metadata associated with the current study.

In another embodiment, the identifying the one or more destination image devices based on metadata associated with the current study may further comprise matching a Retrieve-AETitle DICOM metadata field.

At 846, sending, from the first server to the one or more destination image devices in the at least one enterprise imaging devices, the processed study based on the assembled matched study set.

The sending to the one or more destination image devices may include an enterprise imaging device such as a PACS server, or a MWL server.

In an alternate embodiment, the matched current study metadata may be associated with the matched current study; the matched prior study metadata may be associated with the matched prior study; and the matched prior series metadata may be associated with the matched prior series, wherein the matched current study metadata, the matched prior study metadata, and the matched prior series metadata may be either DICOM format and an HL7 format.

In one embodiment, the processed study may be sent to the one or more destination image devices generally contemporaneously with a patient corresponding to the current study being imaged at the first image device.

Figure 8C:
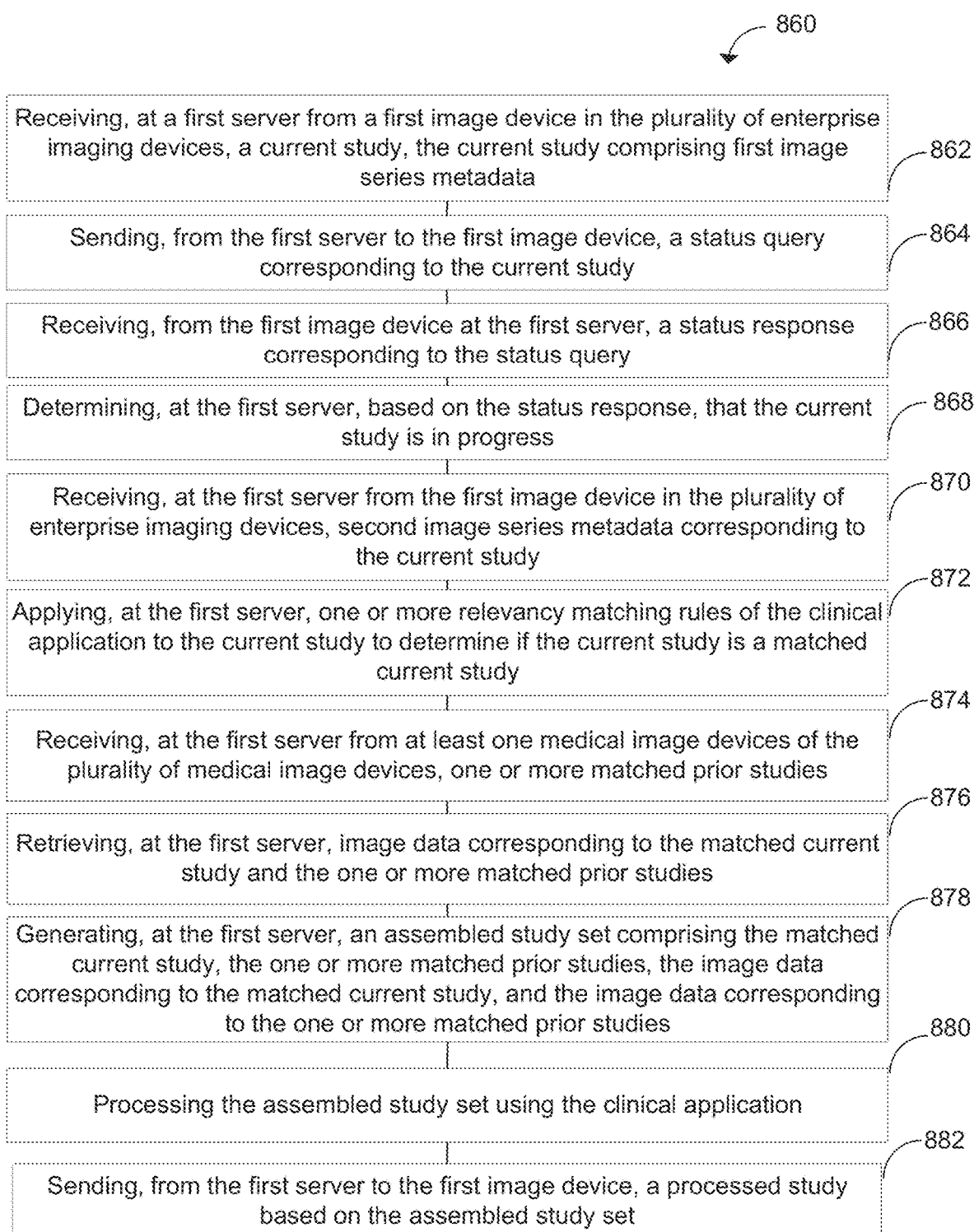
FIG. 8C is another method diagram for processing medical data.

Referring next to FIG. 8C, there is shown a method diagram 860 for processing medical data. The method 860 may be for determining that a current study that is received at a platform has been completely collected at an image acquisition device 112 in FIG. 1A.

At 862, receiving, at a first server from a first image device in the plurality of enterprise imaging devices, a current study, the current study comprising first image series metadata. The current study may be received from at least one of a Picture Archiving and Communication System (PACS) server and a MWL server.

In one embodiment, the current study may be pushed (or auto-forwarded) to the first server from a PACS server or a MWL server, or alternatively from an image acquisition device.

In another embodiment, the first server may send a polling request to the PACS server, the polling request is for a new current study. Further, the first server may send a second polling request for a new current study to a MWL server.

At 864, sending, from the first server to the first image device, a status query corresponding to the current study.

At 866, receiving, from the first image device at the first server, a status response corresponding to the status query.

At 868, determining, at the first server, based on the status response, that the current study is in progress.

In one embodiment determining that the current study is in progress may further comprise determining that the current study has changed during a polling threshold. This may be based upon a comparison of the current study metadata, including series data associated with the current study. The polling interval and the polling threshold may be configurable.

In an alternate embodiment, determining that the current study is in progress may further comprise receiving, at the first server, the second image series metadata; and applying, at the first server, one or more relevancy matching rules to the second image series metadata.

At 870, receiving, at the first server from the first image device in the plurality of enterprise imaging devices, second image series metadata corresponding to the current study.

In one embodiment, the first image series and the second image series are collected by the first image device; and the second image series metadata is collected by the first image device after the first image series metadata is received at the first server. In other words, the second image series may be completed at the image acquisition device after the first study including the first series are received at the platform.

At 872, applying, at the first server, one or more relevancy matching rules of the clinical software application to the current study to determine if the current study is a matched current study.

At 874, receiving, at the first server from at least one enterprise imaging devices of the plurality of enterprise imaging devices, one or more matched prior studies.

At 876, retrieving, at the first server, image data corresponding to the matched current study and the one or more matched prior studies.

At 878, generating, at the first server, an assembled study set comprising the matched current study, the one or more matched prior studies, the image data corresponding to the matched current study, and the image data corresponding to the one or more matched prior studies.

At 880, processing the assembled study set using the clinical software application.

At 882, sending, from the first server to the first image device, a processed study based on the assembled study set.

Figure 9A:
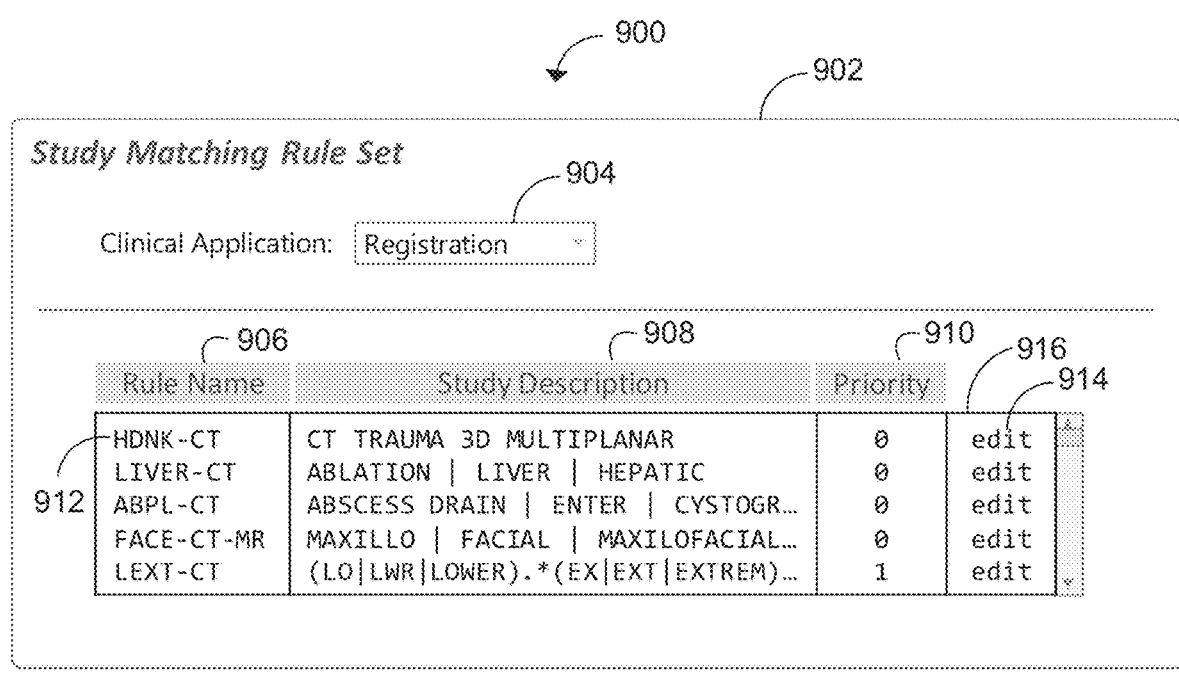
FIG. 9A is a user interface showing an interface for changing a rule set associated with a clinical software application.

Referring next to FIG. 9A, there is shown a user interface diagram 900 showing an interface 902 for viewing rules and changing a rule set associated with a clinical software application. The user interface 902 has a clinical software application selector 904, a rule listing table 916 having rows corresponding to a study matching rule 912 of a platform, and columns including a rule name 906, a study description 908, a priority 910, and an edit selector 914 that enables a user to edit the study matching rule itself.

A user using user interface 902 may select one or more current study matching rules 914 for the clinical software application 904 to add them as relevancy matching rules to determine whether a received current study is a matched current study. The user interface may automatically generate a clinical software application configuration as shown in FIGS. 7B-7D.

Figure 9B:
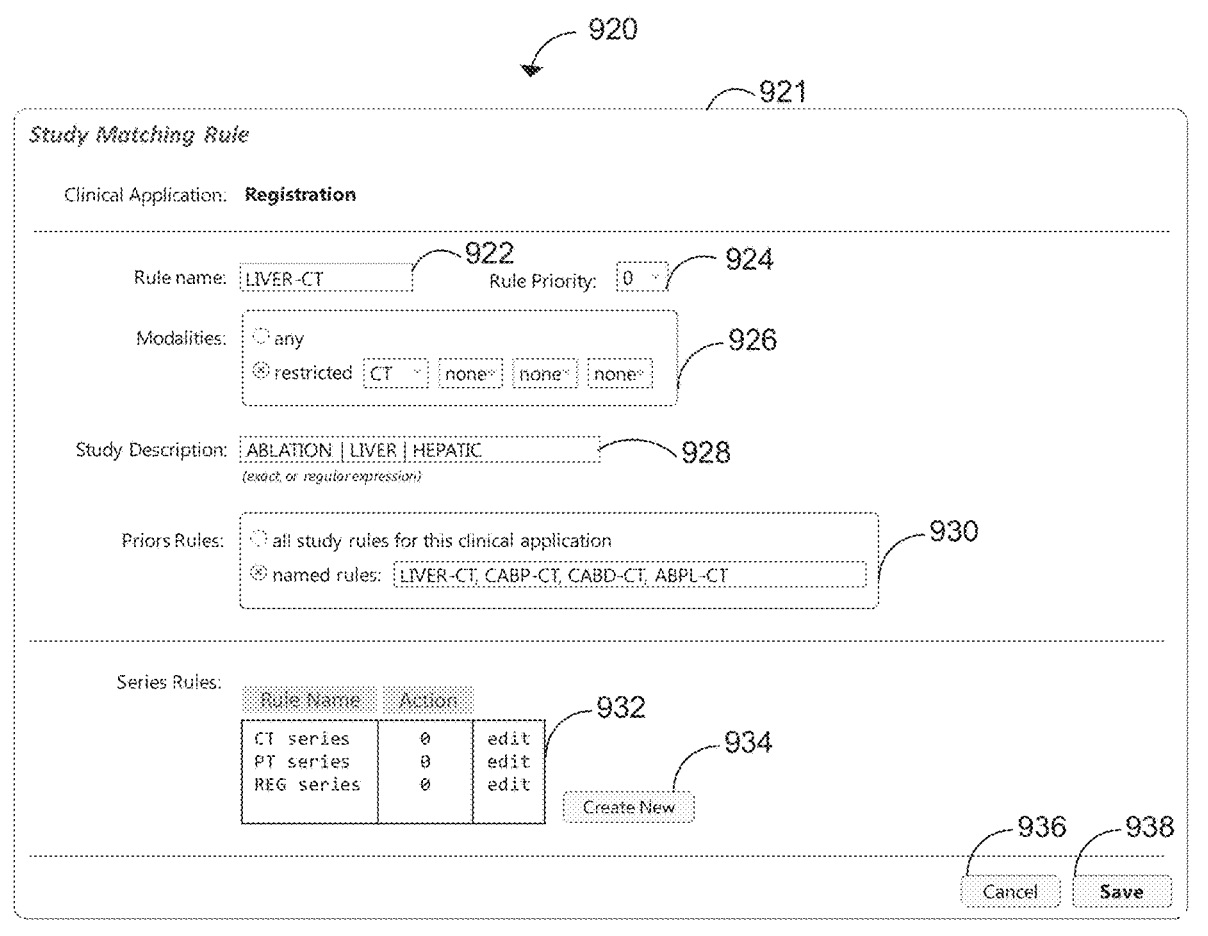

By clicking edit, a user may be presented another user interface for editing the study matching rule as shown in FIGS. 9B and 9C.

Referring next to FIG. 9B, which shows a user interface diagram 920 showing an interface 921 for viewing and changing a study matching rule. The user interface 921 has a rule name field 922, a rule priority field 924, a modality matching field 926, a study description field 928, a prior rules selector 930, a current series rule selector 932, a new series rule create button 934 (which may bring a user who selects it to the user interface in FIG. 9D), a cancel button 936 and a save button 938.

The study description matching field 928 and the prior named rules field 930 may support exact matching of field input, or alternatively, may support a user preparing a regular expression to perform pattern matching.

A user may change the rule name 922, and rule priority 924. The rule priority 924 may determine in which order the rule is applied when there are more than one rule associated with a clinical software application based upon the input in interface 921.

A user using user interface 921 may describe one or more types of current studies 928 for matching for the clinical software application. A user may specify which types of modalities 926 may match for the study matching rule. A user may specify one or more prior matching rules 930 for the current rule by name. The prior matching rules and the current matching rules may be used interchangeably, such that a current study matching rule for a clinical software application may also be a prior study matching rule for a different current study matching rule. Further, the user may select one or more series matching rules to determine if the series associated with the current study are matched to a current series. A user may further click 'Create New' button 934 to be taken to an interface such as FIG. 9D to create a new series rule. Finally a user may discard changes in the interface 921 by selecting the cancel button 936, or may save the changes using the Save button 938. The user interface may automatically generate a current rule configuration as shown in FIGS. 7B-7D based on this user input.

Referring next to FIG. 9C, there is shown a user interface diagram 940 showing another interface 941 for changing a study matching rule enabling extended metadata field matching. The interface 941 generally follows the functionality of the interface 921 in FIG. 9B, with additional functionality as described. The interface 941 may include further field matching beyond that shown in FIG. 9B. This may include field matching of other DICOM metadata fields 942, such as Referring Physician's Name 944 as shown. The interface allows a user to identify the field name 944, and identify a matching field for the rule 946. Multiple other DICOM fields 942 may be used, but selection of the Create New button 948. The user interface 941 may automatically generate a current rule configuration as shown in FIGS. 7B-7D based on this user input.

The other DICOM matching field may support exact matching of field input, or alternatively, may support a user preparing a regular expression to perform pattern matching.

Figure 9D:
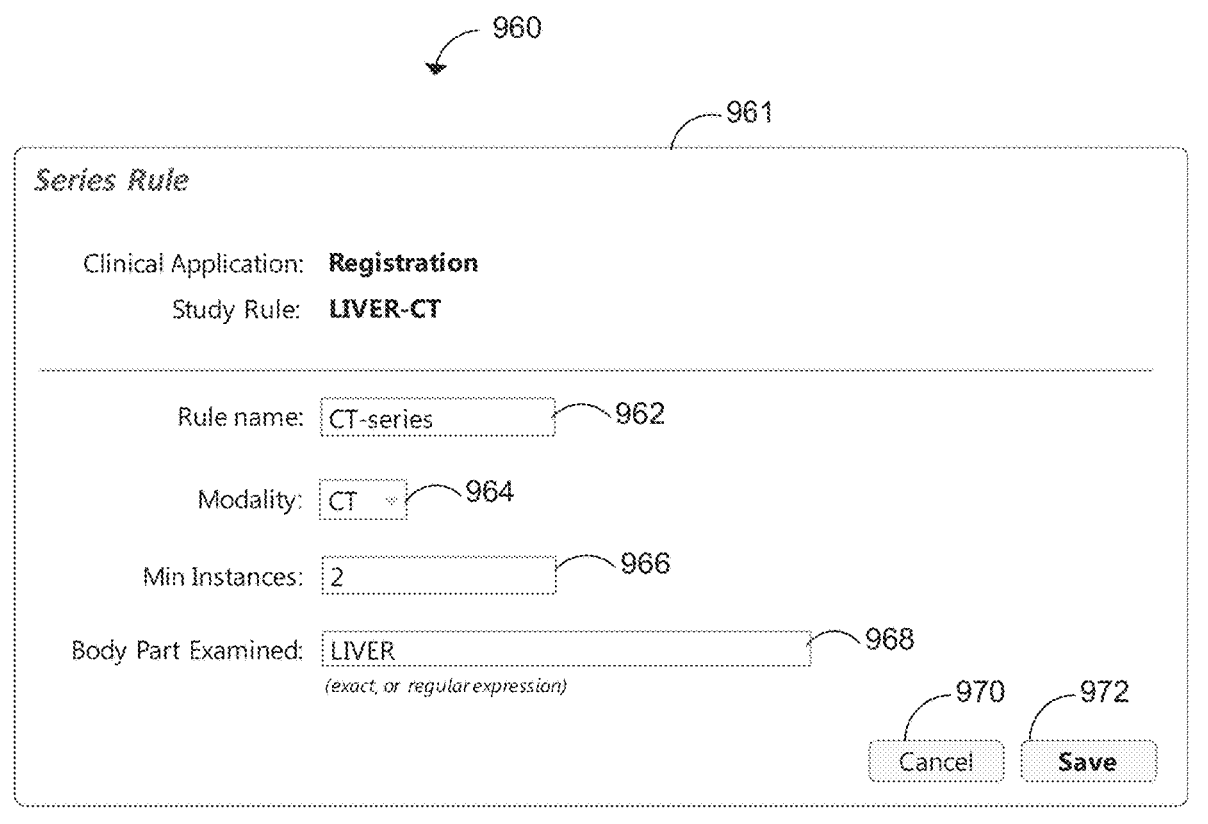

Referring next to FIG. 9D, there is shown a user interface diagram 960 showing an interface 961 for viewing and changing a series rule. The user interface 961 has a rule name field 962, a modality selector 964, a minimum instance field 966, and a body part label field 968, a cancel button 970 and a save button 972.

The series editing interface 961 allows a user to create a series matching rule by specifying a rule name 962, a modality of the series 964 for matching, a minimum instance count (or minimum image count) 966, and a matching body part name 968. The minimum image count 966 may specify that a minimum number of images must be received as a condition to the matching rule matching the series.

The cancel button 970 may discard changes made in the series matching rule interface, and the save button 972 may save the changes.

The user interface 961 may automatically generate a current rule configuration as shown in FIGS. 7B-7D based on this user input.

We claim:

1. A computer-implemented method of reducing network traffic in a communication network configured to process a plurality of medical images using a plurality of clinical software applications, the method comprising:
   receiving, using a network device from a first image system in the plurality of medical image systems, an initial portion of a current study collected by an image acquisition device, the initial portion comprising first image series metadata, wherein the first image series metadata is collected at a first image series collection event by the image acquisition device, and wherein a transmission size of the first image series metadata is less than a transmission size of image data associated with the initial portion, and wherein the first image series metadata of the initial portion is separate from the image data associated with the initial portion;
   determining, by a processor in communication with the network device, that the collection of the current study at the image acquisition device is in progress based on the first image series metadata;
   receiving, using the network device from the first image system in the plurality of medical image systems, a subsequent portion of the current study comprising second image series metadata corresponding to the current study, wherein the second image series metadata is collected at a subsequent image series collection event by the image acquisition device, wherein the first image series collection event occurs before the subsequent image series collection event, and wherein a transmission size of the second image series metadata is less than a transmission size of image data associated with the subsequent portion, and wherein the second image series metadata of the subsequent portion is separate from the image data associated with the subsequent portion;
   applying, at the processor, one or more relevancy matching rules associated with the plurality of clinical software applications to the current study, the current study comprising current study metadata, to determine if the current study is a matched current study and to determine a matching clinical software application in the plurality of clinical software applications in lieu of a comparison between image data associated with the matched current study;
   retrieving, using the network device, the image data corresponding to the matched current study;
   generating, by the processor, an assembled study set comprising the matched current study, and the image data corresponding to the matched current study;
   generating, by the processor, a metadata-based comparison for determining that the current study is completely assembled by comparing the first image series metadata collected at the first image series collection event and the second image series metadata collected at the subsequent image series collection event in lieu of a comparison between image data associated with the first image series and image data associated with the second image series;
   determining, by the processor, that the current study is completely assembled based on the metadata-based comparison of the first image series metadata collected at the first image series collection event and the second image series metadata collected at the subsequent image series collection event;
   processing, by the processor, based on the determining that the current study is completely assembled, the assembled study set using the matching clinical software application to generate a processed study comprising clinical information about the current study based on the completed assembled study; and
   sending, by the network device, to the first image system, the processed study based on the assembled study set.

2. The method of claim 1, wherein the determining, at the processor, that the current study is in progress further comprises:
   receiving, one or more additional series metadata corresponding to the current study;
   determining, based on a count of the one or more additional series metadata corresponding to the current study, that the current study is in progress.

3. The method of claim 1, wherein the first image series metadata is pushed to the network device from at least one of the group of a PACS server, a Modality Worklist, and a medical image device; and wherein the at least one of the group of the PACS server, the Modality Worklist, and the medical image device pushes the second image series metadata.

4. The method of claim 1, wherein the determining, at the processor, that the current study is in progress further comprises:
   sending, from the network device to the first image system, one or more status queries;
   receiving, from the first image system at the network device, one or more status responses corresponding to the one or more status queries; and
   determining, based on the one or more status responses, that the current study is in progress.

5. The method of claim 4, wherein:
the one or more status queries comprise one or more polling requests; and
the one or more polling requests are sent from the network device to at least one of the group of a PACS server and a Modality Worklist; and
the determining, based on one or more polling responses corresponding to the one or more polling requests, that the current study is in progress is based on a change to the current study during a change threshold period of time.

6. The method of claim 5, wherein the one or more polling requests are recurrently sent at a polling interval.

7. The method of claim 6, further comprising:
determining, based on the polling response, that the current study has not changed at an expiry of the change threshold and that the current study is complete.

8. The method of claim 7, wherein the polling interval and the change threshold are configurable.

9. The method of claim 8, wherein the polling interval and the change threshold are selected based on a performance metric of the network device or the processor.

10. The method of claim 6, wherein the determining, at the processor, that the current study is in progress further comprises:
receiving, at the network device, the second image series metadata; and
applying, at the processor, one or more relevancy matching rules to the second image series metadata.

11. The method of claim 1, wherein:
the first image series metadata corresponds to a first series of medical images collected by the first image system;
the second image series metadata corresponds to a second series of medical images collected by the first image system; and
the second image series metadata is collected by the first image system after the first image series metadata is received at the network device.

12. The method of claim 1, further comprising:
receiving, at the network device from the first image system in the plurality of medical image systems, third image series metadata corresponding to the matched current study.

13. The method of claim 1, further comprising:
receiving, at the network device of the processing server from at least one medical image systems of the plurality of medical image systems, one or more matched prior studies;
wherein the retrieving, using the network device the processing server, further comprises retrieving image data corresponding to the one or more matched prior studies; and
wherein the assembled study set further comprises the one or more matched prior studies and the image data corresponding to the one or more matched prior studies.

14. The method of claim 1, wherein the image data corresponding to the matched current study comprises at least one selected from the group of: X-ray Plain Film (PF) data, digital X-ray data, cardiology imaging device data, Computed Tomography (CT) data, ultrasound image data, nuclear medicine imaging data including Positron-Emission Tomography (PET) data, Veterinary imaging device data, Magnetic Resonance Imaging (MRI) data, and mammographic image data.

15. The method of claim 1, wherein:
the first image series metadata comprises a timestamp of the first image series collection event;
the second image series metadata comprises a timestamp of the second image series collection event; and
the metadata-based comparison of the first image series metadata collected at the first image series collection event and the second image series metadata collected at the subsequent image series collection event comprises a comparison of the timestamp of the first image series collection event and the timestamp of the second image series collection event.

16. A computer-implemented system of reducing network traffic in a communication network configured to process a plurality of medical images using a plurality of clinical software applications, the system comprising:
a processing server, the processing server comprising:
a memory;
a network device; and
a processor in communication with the memory and the network device, the processor configured to:
receive, at the network device from a first image system in the plurality of medical image systems, an initial portion of a current study, the current study collected by an image acquisition device, the initial portion comprising first image series metadata, wherein the first image series metadata is collected at an initial image series collection event by the image acquisition device, and wherein a transmission size of the first image series metadata is less than a transmission size of image data associated with the initial portion, and wherein the first image series metadata of the initial portion is separate from the image data associated with the initial portion;
determine that the collection of the current study at the image acquisition device is in progress based on the first image series metadata;
receive, at the network device from the first image system in the plurality of medical image systems, a subsequent portion of the current study comprising second image series metadata corresponding to the current study, wherein the second image series metadata is collected at a subsequent image series collection event by the image acquisition device, wherein the first image series collection event occurs before the subsequent image series collection event and wherein a transmission size of the second image series metadata is less than a transmission size of image data associated with the subsequent portion, and wherein the second image series metadata of the subsequent portion is separate from the image data associated with the subsequent portion;
apply one or more relevancy matching rules associated with the plurality of clinical software applications to the current study, the current study comprising current study metadata, to determine if the current study is a matched current study and to determine a matching clinical software application in the plurality of clinical software applications in lieu of a comparison to image data associated with the current study;
retrieve, using the network device, the image data corresponding to the matched current study;
generate an assembled study set comprising the matched current study, and the image data corresponding to the matched current study;
generate a metadata-based comparison for determining that the current study is completely assembled by comparing the first image series metadata collected at the first image series collection event and the second image series metadata collected at the subsequent image series collection event in lieu of a comparison between image data associated with the first image series and image data associated with the second image series;

determine that the current study is completely assembled based on the metadata-based comparison of the first image series metadata collected at the first image series collection event and the second image series metadata collected at the subsequent image series collection event;

process, based on the determination that the current study is completely assembled, the assembled study set using the matching clinical software application to generate a processed study comprising clinical information about the current study based on the completed assembled study; and send, from the network device to the first image system, the processed study based on the assembled study set.

17. The system of claim 16 wherein the processor is further configured to:
receive, one or more additional series metadata corresponding to the current study;
determine, based on a count of the one or more additional series metadata corresponding to the current study, that the current study is in progress.

18. The system of claim 16 wherein the first image series metadata is pushed to the processing server from at least one of the group of a PACS server, a Modality Worklist, and a medical image device; and wherein the at least one of the group of the PACS server, the Modality Worklist, and the medical image device pushes the second image series metadata.

19. The system of claim 16, wherein the processor is further configured to:
send, from the processing server to the first image system, one or more status queries;
receive, from the first image system at the processing server, one or more status responses corresponding to the one or more status queries; and
determine, based on the one or more status responses, that the current study is in progress.

20. The system of claim 19, wherein:
the one or more status queries comprise one or more polling requests; and
the one or more polling requests are sent from the processing server to at least one of the group of a PACS server and a Modality Worklist; and
the determining, based on one or more polling responses corresponding to the one or more polling requests, that the current study is in progress is based on a change to the current study during a change threshold period of time.

21. The system of claim 20, wherein the one or more polling requests are recurrently sent at a polling interval.

22. The system of claim 20, wherein the processor is further configured to:
determine, based on the polling response, that the current study has not changed at an expiry of the change threshold and that the current study is complete.

23. The system of claim 22 wherein the polling interval and the change threshold are configurable.

24. The system of claim 23 wherein the polling interval and the polling threshold are selected based on a performance metric of the processing server.

25. The system of claim 16 wherein the processor is further configured to determine that the matched current study is complete by:
receiving, at the processing server, the second image series metadata; and
applying, at the processing server, one or more relevancy matching rules to the second image series metadata.

26. The system of claim 16 wherein:
the first image series metadata corresponds to a first series of medical images collected by the first image system;
the second image series metadata corresponds to a second series of medical images collected by first image system; and
the second image series metadata is collected by the first image system after the first image series metadata is received at the processing server.

27. The system of claim 16, wherein the processor is further configured to:
receive, at the network device from the first image system in the plurality of medical image systems, third image series metadata corresponding to the matched current study.

28. The system of claim 16, wherein the processor is further configured to:
receive at the network device of the processing server from at least one medical image systems of the plurality of medical image systems, one or more matched prior studies;
wherein the retrieving at the network device of the processing server further comprises retrieving image data corresponding to the one or more matched prior studies; and
wherein the assembled study set further comprises the one or more matched prior studies and the image data corresponding to the one or more matched prior studies.

29. The system of claim 16, wherein the image acquisition device comprises at least one selected from the group of: an X-ray Plain Film (PF) imaging device, a digital X-ray imaging device, a cardiology imaging device, a Computed Tomography (CT) device, an ultrasound imaging device, a nuclear medicine imaging device including a Positron-Emission Tomography (PET) imaging device, a Veterinary imaging device, a Magnetic Resonance Imaging (MRI) device, and a mammographic imaging device.

30. The system of claim 16, wherein:
the first image series metadata comprises a timestamp of the first image series collection event;
the second image series metadata comprises a timestamp of the second image series collection event; and
the metadata-based comparison of the first image series metadata collected at the first image series collection event and the second image series metadata collected at the subsequent image series collection event comprises a comparison of the timestamp of the first image series collection event and the timestamp of the second image series collection event.

\* \* \* \* \*